US011590185B2

(12) United States Patent
Kim et al.

(10) Patent No.: US 11,590,185 B2
(45) Date of Patent: Feb. 28, 2023

(54) **ANTIOXIDANT COMPOSITION COMPRISING *SARGASSUM SERRATIFOLIUM* EXTRACT OR FRACTION THEREOF AS ACTIVE INGREDIENT**

(71) Applicant: PUKYONG NATIONAL UNIVERSITY INDUSTRY-UNIVERSITY COOPERATION FOUNDATION, Busan (KR)

(72) Inventors: Hyeung-Rak Kim, Busan (KR); Su-Jin Lim, Busan (KR); Mi-Sung Kwon, Busan (KR); Min-Sup Lee, Busan (KR)

(73) Assignee: Pukyong National University Industry-University Corporation Foundation, Busan (KR)

( * ) Notice: Subject to any disclaimer, the term of this patent is extended or adjusted under 35 U.S.C. 154(b) by 281 days.

(21) Appl. No.: 17/036,456

(22) Filed: Sep. 29, 2020

(65) Prior Publication Data

US 2021/0060104 A1    Mar. 4, 2021

Related U.S. Application Data

(62) Division of application No. 16/078,401, filed as application No. PCT/KR2016/003975 on Apr. 18, 2016, now abandoned.

(30) Foreign Application Priority Data

Dec. 21, 2015 (KR) .................. 10-2015-0182907

(51) Int. Cl.
*A61K 36/03* (2006.01)
*A61Q 19/00* (2006.01)
(Continued)

(52) U.S. Cl.
CPC .............. *A61K 36/03* (2013.01); *A23L 17/60* (2016.08); *A23L 33/10* (2016.08); *A61K 8/9711* (2017.08);
(Continued)

(58) Field of Classification Search
CPC ...................................................... A61K 36/03
See application file for complete search history.

(56) References Cited

U.S. PATENT DOCUMENTS 5,165,933 A    11/1992 Oishi

FOREIGN PATENT DOCUMENTS

KR    10-2010-0131809 A    12/2010
KR    10-2011-0006444 A    1/2011
(Continued)

OTHER PUBLICATIONS

Liu et al., "Towards a better understanding of medicinal uses of the brown seaweed *Sargassum* in Traditional Chinese Medicine: a phytochemical and pharmacological review," Journal of Ethnopharmacology 142:591-619, 2012.*
(Continued)

*Primary Examiner* — Rosanne Kosson
(74) *Attorney, Agent, or Firm* — FisherBroyles, LLP; Joseph Hyosuk Kim

(57) ABSTRACT

The present invention relates to an antioxidant composition and, more specifically, to an antioxidant composition including a *Sargassum serratifolium* extract or a fraction thereof as an active ingredient, in which the antioxidant composition is a useful material (substance) that can be added to medicines, cosmetics, foods, animal feeds, and the like. The present invention also relates to a pharmaceutical composition for preventing or treating eye diseases, a food composition for alleviating eye diseases, and a health functional food, each
(Continued)

of which includes a *Sargassum serratifolium* extract or a compound separated therefrom as an active ingredient.

4 Claims, 7 Drawing Sheets

(51) Int. Cl.
    *A23L 17/60*     (2016.01)
    *A23L 33/10*     (2016.01)
    *A61K 8/9711*     (2017.01)
    *A61Q 19/08*     (2006.01)

(52) U.S. Cl.
    CPC ............. *A61Q 19/00* (2013.01); *A61Q 19/08* (2013.01); *A23V 2002/00* (2013.01)

(56) References Cited

FOREIGN PATENT DOCUMENTS

| | | |
|---|---|---|
| KR | 10-2012-0074498 A | 7/2012 |
| KR | 10-2013-0142424 A | 12/2013 |
| KR | 10-1589002 B1 | 1/2016 |

OTHER PUBLICATIONS

Gwon, Wi-Gyeong et al., "Sargaquinoic Acid Inhibits TNF-α-Induced NF-κB Signaling, Thereby Contributing to Decreased Monocyte Adhesion to Human Umbilical Vein Endothelial Cells (HUVECs)," Journal of Agriculture and Food Chemistry, vol. 63, pp. 9053-9061, 2015.

Kusumi, Takenori et al., Structures of New Plastoquinones from the Brown Alga *Sargassum serratifolium*, Chemistry Letters, pp. 277-278, 1979.

Ham, Young Min et al., "Chemical Constituents from Sargassum micracanthum and Antioxidant Activity," International Journal of Pharmacology, vol. 6, No. 2, pp. 147-151, 2010.

Yende, Subhash R., "Therapeutic potential and health benefits of *Sargassum* species," Pharmacognosy Reviews, vol. 8, No. 15, pp. 1-7, 2014.

KIPRIS machine translation into English of Hanbul Cosmetics Co. Ltd. KR 1010358580000 B 2011.

\* cited by examiner

ANTIOXIDANT COMPOSITION COMPRISING SARGASSUM SERRATIFOLIUM EXTRACT OR FRACTION THEREOF AS ACTIVE INGREDIENT

CROSS REFERENCE TO RELATED APPLICATIONS

This application is a divisional of U.S. application Ser. No. 16/078,401, filed Aug. 21, 2018, pending, which is a U.S. National Phase of International Application No. PCT/KR2016/003975, filed Apr. 18, 2016, the contents of each incorporated herein by reference in its entirety.

TECHNICAL FIELD

The present invention relates to an antioxidant composition, and more particularly to an antioxidant composition including a *Sargassum serratifolium* extract or fraction thereof as an active ingredient, which is a useful substance (material) that can be added to medicines, cosmetics, foods, animal feeds and the like. The present invention also relates to a pharmaceutical composition for preventing or treating eye diseases, a food composition for alleviating eye diseases, and a health functional food, each of which includes a *Sargassum serratifolium* extract or a compound separated therefrom as an active ingredient.

BACKGROUND ART

Anti-oxidation refers to the prevention of various oxidations which occur in the body. Lipids present as biological membranes and lipoproteins are attacked by free radicals in the body so as to form various kinds of peroxides. Such peroxides, decomposition products, and like are highly reactive to change the structure and function of the surrounding biomolecules, thereby resulting in the aging phenomenon and various chronic diseases.

The body contains various antioxidant defense mechanisms which can neutralize such free radicals to protect the body. Human diseases and aging are caused by the oxidation of $O_2$ (superoxide), NO (nitric oxide), $NO_2$ (nitrogen dioxide), OH (hydroxyl), ROO (proxyl), RO (alkoxyl), $HO_2$ (hydroperoxyl) radical, and the like that occur during metabolism in the body. As a mean of protecting the living body from free radicals such as these harmful radicals, superoxide dismutase (SOD), an antioxidant enzyme, reduces superoxide radicals to $H_2O_2$ in the body. For $H_2O_2$ caused herein, antioxidant enzymes such as catalase (CAT), glutathione peroxidase (GSH-px) and antioxidants such as vitamin C, vitamin E, and glutathione remove the free radicals to protect the body against oxidative damage.

However, when the antioxidant defense system is weak to such an extent that cannot control the free radical generation, the oxidative stress and damage of tissues are promoted, and the excess free radicals and lipid peroxides generated in the body increase damage caused by oxidative stress such as protein oxidation and DNA damage. Currently reported, in 2003 the leading causes of death in South Korea were cancer, cerebrovascular disease, cardiovascular disease, and diabetes in order (Korea National Statistical Office: The cause of death statistics, 2003 and Annual Report of on the Cause of Death Statistics. Korea National Statistical Office, 2004). It is known that reactive oxygen species (ROS) may be the main cause of chronic degenerative diseases such as cardiovascular disease, diabetes, cancer, degenerative neuropathy, and aging, and antioxidants may remove the reactive oxygen species to help to prevent chronic degenerative diseases.

The active oxygens ($O_2^-$, $H_2O_2$, OH and $^1O_2$) generated during the human physiological process are highly reactive, and the free radical reactions caused by them results in the destruction of major macromolecules including lipids (Davies, K J A and Goldberg, A L., J. Biol. Chem., 262, pp. 8220-8226, 1987). Their generation is increased by various causes that result in abnormalities in normal metabolism, photosensitization reaction, drug metabolism, and another cell metabolism. Living organisms are always exposed to the harmful effects of free radical reactions induced by them.

In particular, as cells age, harmful effects due to these harmful radicals are continuously accumulated, resulting in diseases related to various adult diseases, according to aging, such as cancer, atherosclerosis, heart disease, skin aging, and eye diseases, as well as overall cell aging. Thus, they are suggested as a cause of human disease and aging.

Meanwhile, eyes are affected by oxidative stress due to ultraviolet rays, radiation, smoking, environmental pollution of living bodies, or systemic oxidative stress due to foreign substances in the blood in the body. In the eye tissue, reactive oxygen species (ROS) are generated by respiration, redox enzymes, and photochemical reactions in the mitochondria. In the mitochondrial electron transport system in cells, electrons received from NADH or succinate are transported by step along with each electron transport complex, resulting in an $O_2$ reduction to become water. However, when electrons are released at the intermediate stage of the electron transport system to be immediately transferred to oxygen, superoxide ($O_2$) is formed non-enzymatically. Nitric oxide synthase (NOS) is converted into L-arginine L-citrulline, which produces nitric oxide. This nitric oxide reacts with superoxide to generate highly reactive peroxynitrite (ONOOK). Further, photosensitizers such as riboflavin generate superoxide, hydroxyl radical, hydrogen peroxide ($H_2O_2$) and the like by photochemical reaction.

The eye tissues include antioxidant enzymes such as superoxide dismutase (SOD) including copper (Cu), zinc (Zn), and manganese (Mn), catalase, and glutathione peroxidase containing selenium (Se), lipid-soluble antioxidant compounds such as tocopherol and carotenoids, and water-soluble antioxidants such as ascorbic acid and reduced glutathione, which are involved in the removal of active oxygen. Further, the eye tissues include glutathione reductase involved in the reduction of oxidized glutathione, thioredoxin and ascorbic acid free radical enzyme which removes ascorbic acid free radicals.

It is known that oxidative stress, which is caused by breaking the balance between the production system and the scavenging system, plays a critical role in the eye tissues and eye diseases. The retina of eyes is a tissue that has a high metabolic rate in the human body, causing a massive amount of oxidative stress. Further, eyes are exposed to high-energy ultraviolet rays, thereby producing a significant amount of active oxygen, which is highly reactive to result in fatal damage such as macular degeneration.

Age-related macular degeneration (hereinafter, referred as to "AMD") is the most active subject among studies about eye diseases. It is reported that more than 8 million people now have dry AMD, a type of this disease in the United States, and more than 3 million people are blinded by the disease each year. The several causes of disease include the production of reactive oxygen derivatives due to excessive oxygen use, accumulation of lipofuscin-retinoid derivatives (bisretinylethanolamine (A2E)), and oxidation by light, but the specific mechanism and treatment methods are not yet known (Zarbin, 2004, Arch Ophthalmol 122, 598-614; Kasahara et al., 2005, Invest Ophthalmol Vis Sci 46, 3426-3434).

The light energy information received by the eye passes through the G-protein coupled receptor (GPCR) signal transferring process, thereby closing the cation channel involved in cGMP, and thus the visual cell becomes electrically polarized so that the information is transmitted to the brain in the form of electric energy. The retinal is changed from 11-cis structure to all-trans structure by light but is again regenerated in 11-cis structure by several proteins and enzymatic reactions. Thus, a series of reactions that the retinal reacts with light and are recycled by enzymes is called the visual cycle or retinoid cycle of the eye. The retinal reacted with light in the visual cell is hydrolyzed to be transferred to the retinal pigment epithelium so that the retinal becomes a substrate for the series of reactions. The recycling of retinal in the eye is a critical factor for continuous viewing of vertebrates.

Photoreceptor cells in the retina are essential optic neurons that accept stimulation of light to convert into electrical signals. Rhodopsin in photoreceptor cells includes an optic and 11-cis-retinal (hereinafter, simply abbreviated as "11cRAL"). The 11cRAL passes through the interphotoreceptor matrix and is then transported to photoreceptor cells. Then, the 11cRAL binds to the opsin protein to form a visual purple called rhodopsin. Photoreceptor cells with rhodopsin are critical for sight in the dark because they may capture even tiny amounts of light. In rhodopsin, photoactivation causes the 11cRAL to be decomposed into all-trans-retinal (hereinafter, simply abbreviated as 'atRAL') and opsin. The atRAL generated herein is gradually reduced to 11cRAL by a visual cycle generated in photoreceptor cells and retinal pigment epithelium. Then, the 11cRAL binds to the opsin to re-synthesize rhodopsin (Jin M, et al., Cell, 2005).

The atRAL and 11cRAL are intermediate metabolites of the visual cycle and are aldehyde-type compounds, which may induce excessive oxidative stress in cells so that they are strictly controlled by several enzymes in each step of the visual cycle. Mutations or dysfunctions or overexposure to the light of enzymes responsible for the visual cycle result in over-production of atRAL and accumulation of atRAL in photoreceptor cells, thereby leading to the death of photoreceptor cells. Patients with visual impairment have gene-mutation of enzymes which play critical roles in the visual cycle such as atROL dehydrogenase, which reduces atRAL to all-trans-retinol (hereinafter, simply abbreviated as "atROL") and ATP-binding cassette sub-family A member 4 (Abca4) and interphotoreceptor retinoid binding protein (IRBP), which aid retinol migration between photoreceptor cells and retinal pigment epithelium, and thus photoreceptor cells in the retina is degraded (Busskamp V, et al., Science, 2010; Allikmets R, et al. Science, 1997; Jin M, et al., Cell, 2005; Jin M, et al. The Journal of Neuroscience, 2009; Maeda A, et al. The Journal of biological chemistry, 2009).

In addition, the mouse animal model confirmed that the genetic defect of each enzyme increases the production of atRAL in the retina. It is thus considered that the regulation of atRAL is very critical in optic nerve tissues. 661W cells are mouse-derived photoreceptor cells, which have been widely used to study optic nerve degeneration, optic nerve protection, and the like (Tan E, et al., Investigative ophthalmology & visual science, 2004). In particular, it has been studied mainly for the response to oxidative stress such as the stimulation of ultraviolet rays and hydrogen peroxide as well as the protective effect on the optic nerve of various compounds (Kanan Y, et al., Cell Mol Neurobiol, 2015; Krishnamoorthy R R, et al., The Journal of Biological Chemistry, 1999).

Accordingly, studies have been conducted on finding a candidate substance which is expected to be useful in various diseases caused by oxidative damage by inhibiting the free radical reaction in the body due to reactive oxygen metabolites or removing harmful active oxygen accumulated in the human body.

Many studies have been actively conducted to prepare safe and powerful antioxidants by separating components with antioxidative activity from natural products all over the world. Until now, studies and reports have been conducted on various natural antioxidants such as soybean (Duh et al., 1997), oilseed (Deiana et al., 1999), herb (Kitts et al., 2000), tea (Roedig-Penman and Gordon, 1997), fruit of strawberries (Wang and Jiao, 2000), ginkgo extract (Gohil et al., 2000), ginseng extract (Keum et al., 2000), fruits and vegetables (Cao et al., 1996; Wang et al., 1996, Brown and Rice-Evans, 1998).

In addition, it is reported that resveratrol, which is abundant in the grape skin, is antioxidant to decrease the death of rat pheochromocytoma (PC12) cells induced by reactive oxygen species (M. V. Clement et al., 1998).

However, there are many antioxidants in the natural world, which have not yet been identified. If these new substances are discovered, they can be used as useful materials for foods, medicines, and cosmetics.

Accordingly, the present inventors have searched for a natural substance having excellent antioxidative activity without any side effect on the living body and focused on *Sargassum serratifolium*. Thus, the present inventors examined the antioxidative effect of *Sargassum serratifolium*. As a result, the present inventors confirmed that a *Sargassum serratifolium* extract and fraction thereof has excellent scavenging ability of nitric oxide and intercellular reactive oxygen species, DPPH radical scavenging activity, ABTS cation scavenging activity, and hydroxyl radical (—OH) scavenging activity, thereby completing the present inventions.

In addition, the present inventors have examined the protective effect of mouse-derived 661W photoreceptor cells using the *Sargassum serratifolium* extract and the compounds separated therefrom. As a result, it has been found that the experimental group, which is treated with *Sargassum serratifolium* extract and the compounds separated therefrom of the present invention, together with atRAL (oxidative stress inducer) shows a significant increase in cell viability compared to the experimental group treated with atRAL alone and inhibitory effect of reactive oxygen species (ROS) production and malondialdehyde (hereinafter, simply abbreviated as "MDA") peroxide protein production, thereby completing the present invention.

DISCLOSURE

Technical Problem

An object of the present invention is to provide a composition that has excellent antioxidative activity and is stable to the human body over long-term use, using a natural marine algae extract.

Another object of the present invention is to provide a food and feed additive composition that has excellent antioxidative activity and is stable to the human body over long-term use, using a natural marine algae extract.

Still another object of the present invention is to provide a cosmetic composition that has excellent antioxidative activity and is stable to the human body over long-term use, using a natural marine algae extract.

Yet still another object of the present invention is to provide a pharmaceutical composition that is useful for preventing or treating eye disease and is stable to the human body over long-term use, using a natural marine algae extract.

Yet still another object of the present invention is to provide a food composition that is useful for preventing or alleviating eye disease and is stable to the human body over long-term use, using a natural marine algae extract.

Yet still another object of the present invention is to provide a health functional food composition that is useful for preventing or alleviating eye disease and is stable to the human body over long-term use, using a natural marine algae extract.

Technical Solution

In order to achieve the objects, the present invention provides a composition having an antioxidative activity, the composition including a *Sargassum serratifolium* extract or a fraction thereof as an active ingredient.

According to one aspect of the present invention, the extract may be extracted with at least one solvent selected from the group consisting of lower alcohols having 1 to 4 carbon atoms, ethyl acetate, acetone, water, and hexane.

According to one aspect of the present invention, the lower alcohols having 1 to 4 carbon atoms may include ethanol.

According to one aspect of the present invention, the fraction may be a hexane fraction of the *Sargassum serratifolium* extract.

According to one aspect of the present invention, the composition may include a *Sargassum serratifolium* extract or a fraction thereof in a concentration of 0.1 μg/ml to 1000 μg/ml.

According to one aspect of the present invention, the composition may be a pharmaceutical composition, a cosmetic composition, a food composition, or a feed composition.

Further, the present invention is to provide an antioxidant or anti-aging cosmetic composition including a *Sargassum serratifolium* extract or a fraction thereof as an active ingredient.

According to one aspect of the present invention, the extract may be extracted with an ethanol solvent.

According to one aspect of the present invention, the fraction may be a hexane fraction of the *Sargassum serratifolium* extract.

According to one aspect of the present invention, the cosmetic composition may have one formation selected from the group consisting of a toner, a gel, soluble liquid, a milky lotion, a nutrition cream, a massage cream, an essence, an oil-in-water type emulsion, a water-in-oil type emulsion, a paste-like anhydrous product, a solid anhydrous product, an oil dispersion in aqueous phase using small spheres, an ionic lipid vesicle, a nonionic lipid vesicle, ointment, cleansing foam, cleansing water, pack, body oil, oil-in-water type makeup base, water-in-oil type makeup base, foundation, skin cover, lipstick, lip gloss, face powder, twin cake, eyeshadow, mascara, cheek color, and eyebrow pencil.

Further, the present invention is to provide a pharmaceutical composition for preventing or treating an eye disease, the pharmaceutical composition including a *Sargassum serratifolium* extract or a compound separated therefrom as an active ingredient.

According to one aspect of the present invention, the extract may be extracted with an ethanol solvent.

According to one aspect of the present invention, the compound may be sargahydroquinoic acid, sargaquinoic acid, or sagachromenol.

According to one aspect of the present invention, the eye disease may be one selected from the group consisting of age-related macular degeneration, glaucoma, diabetic retinopathy, retinitis pigmentosa, choroidal neovascular membrane, uveitis, myopic degeneration, ocular tumor, central retinal vein occlusion, skin flushing, ocular neovascularization, central serous retinopathy, dry eye syndrome, central retinal artery occlusion, and cystoid macular edema.

Further, the present invention is to provide a food composition for preventing or alleviating an eye disease, the food composition including a *Sargassum serratifolium* extract or a compound separated therefrom as an active ingredient.

According to one aspect of the present invention, the extract may be the *Sargassum serratifolium* ethanol extract, and the compound may be sargahydroquinoic acid, sargaquinoic acid, or sargachromenol.

Further, the present invention is to provide a health functional food for preventing or alleviating an eye disease, the health functional food including a *Sargassum serratifolium* extract or a compound separated therefrom as an active ingredient.

According to one aspect of the present invention, the extract may be the *Sargassum serratifolium* ethanol extract, and the compound may be sargahydroquinoic acid, sargaquinoic acid or sagachromenol.

According to one aspect of the present invention, the food may be one selected from the group consisting of a beverage, meat, chocolate, a food, snack, pizza, ramen, another noodle, a gum, candy, ice cream, an alcoholic beverage, a vitamin complex, and a health supplement food.

According to one aspect of the present invention, the *Sargassum serratifolium* extract or the compound separated therefrom may have an effect of protecting a photoreceptor cell by antioxidative activity.

Advantageous Effects

A *Sargassum serratifolium* extract or a fraction thereof according to the present invention has excellent DPPH radical scavenging activity, ABTS cation scavenging activity, and hydroxyl radical (—OH) scavenging activity as well as the intercellular nitric oxide and reactive oxygen species scavenging ability. Thus, a composition containing it as an active ingredient has an antioxidative activity, which may be useful for functional additive materials for medicines, cosmetics, foods, animal feeds, and the like.

Further, the *Sargassum serratifolium* extract or a compound derived therefrom according to the present invention has an excellent effect of protecting photoreceptor cells on the retina of the eye. Thus, a composition containing it as an active ingredient may be useful for medicine and health functional food materials for preventing, alleviating, or treating eye diseases.

In particular, *Sargassum serratifolium* may be edible as a natural material, so that the composition of the present invention including the extract derived therefrom and fraction or compound derived therefrom has an advantage of safety over long-term use.

BEST MODES

Experimental Example 1

Evaluation of Cytotoxicity of *Sargassum serratifolium* Ethanol Extract and n-Hexane Fraction Thereof of the Present Invention RAW 264.7 cells ($5 \times 10^4$ cells/well) were treated with the *Sargassum serratifolium* ethanol extract or hexane fraction thereof, respectively, of the present invention prepared in Example 1, and cultured in DMEM medium for 24 hours. 95 μl the medium and 5 μl the MTS solution were placed in a 96-well plate and were reacted for 3 hours. Then, the absorbance thereof was measured at 490 nm using a microplate reader. The experiments were repeated three times, and the mean value thereof was used as its measurement value.

Figure 8:
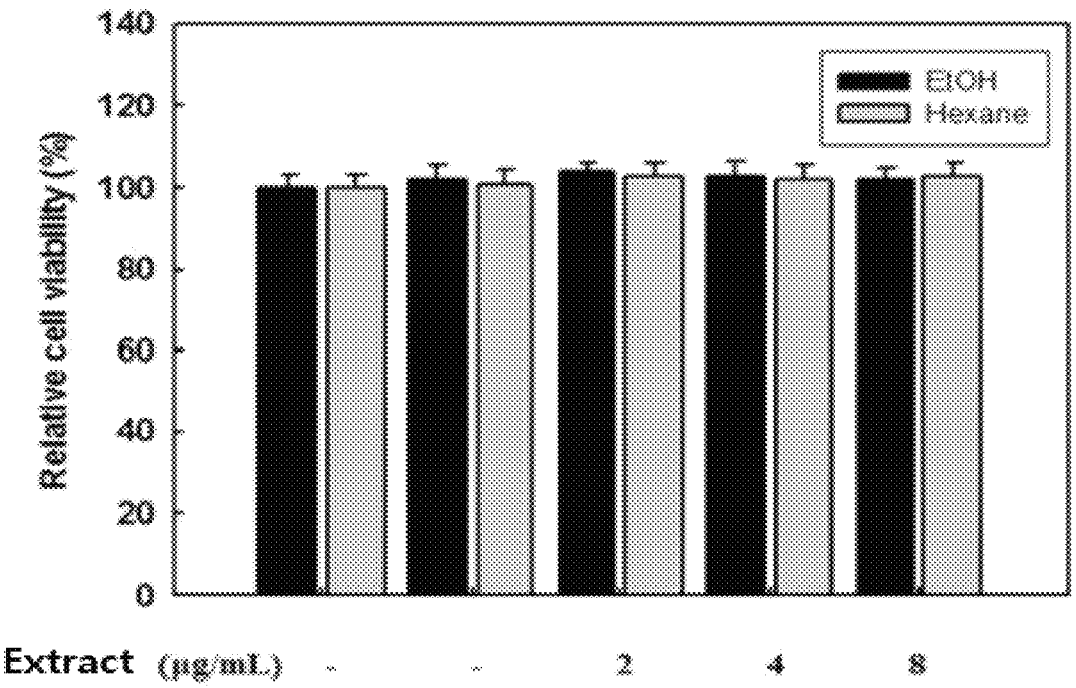
FIG. 8 illustrates the results of measuring the cytotoxicity of macrophage (RAW 264.7) according to treatment concentration of a *Sargassum serratifolium* ethanol extract and hexane fraction thereof of the present invention.

As illustrated in FIG. 8, the results indicate that the cytotoxicity of *Sargassum serratifolium* ethanol extract or hexane fraction thereof of the present invention to the macrophage line (RAW 264.7 cells) did not show up to a concentration of 8 μg/mL.

Experimental Example 2

Antioxidative Activity of *Sargassum serratifolium* Ethanol Extract and n-Hexane Fraction Thereof of the Present Invention Nitric oxide, reactive oxygen species (ROS), antioxidative activity by DPPH method, ABTs antioxidative activity, and hydroxyl radical were measured so as to evaluate the antioxidative activity of *Sargassum serratifolium* ethanol extract and hexane fraction thereof of the present invention prepared in Example 1.

<2-1> Measurement of Nitric Oxide

RAW 264.7 cells ($7 \times 10^4$ cells/well) were inoculated into 96-well plates using DMEM medium. New medium containing samples (*Sargassum serratifolium* ethanol extract or hexane fraction thereof of the present invention prepared in Example 1) and LPS (1 μg/mL) were co-treated and were cultured for 24 hours. The Griess reagent was used, so that the amount of NO produced was measured in the form of $NO^{2-}$ present in the cell culture medium. 100 μL the cell culture supernatant and 100 μL Griess reagent [1% sulfanilamide, 0.1% naphthyl ethylenediamine in 5% phosphoric acid] were mixed and reacted on a 96-well plate for 10 minutes. Then, the absorbance thereof was measured at 540 nm using an ELISA reader. Standard concentration curves were obtained by serial dilution of sodium nitrite ($NaNO_2$).

Figure 9:
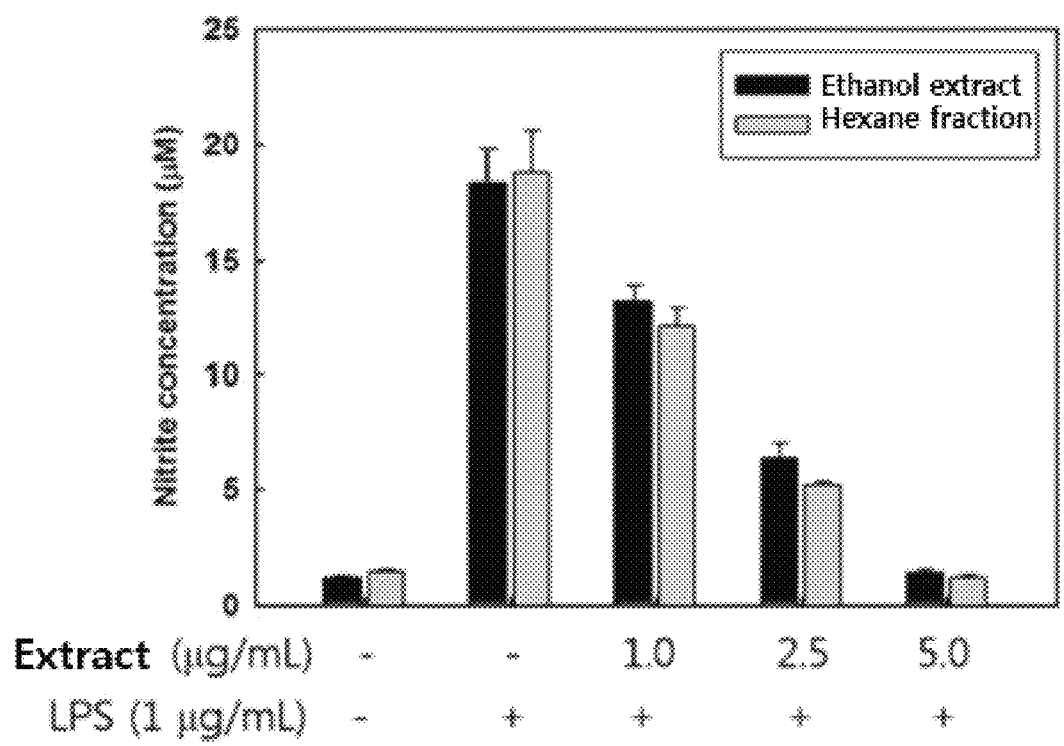
FIG. 9 illustrates the results of measuring LPS-induced nitric oxide production in macrophages according to treatment concentration of a *Sargassum serratifolium* ethanol extract and hexane fraction thereof of the present invention.

As illustrated in FIG. 9, the results indicate that the production of nitric oxide (NO) induced by lipopolysaccharide (LPS) was decreased treatment-concentration dependently in the experimental group treated with a *Sargassum serratifolium* ethanol extract and a hexane fraction thereof in macrophages, respectively. The $EC_{50}$ values of the ethanol extract and hexane fraction were 1.72 μg/mL and 1.51 μg/mL, respectively.

<2-2> Measurement of Intracellular Reactive Oxygen Species

DCFH-DA was used to measure the amount of active oxygen so as to examine the inhibitory effect of the *Sargassum serratifolium* extract on the production of reactive oxygen species (RAW 264.7 cells). Samples (*Sargassum serratifolium* ethanol extract or hexane fraction thereof of the present invention prepared in Example 1) and LPS (1 μg/mL) were co-treated and were cultured for 2 hours. Then, they were treated with 20 μM DCFH-DA and were cultured for 30 minutes. Thereafter, the cell culture supernatant was collected and measured by spectrofluorometry at an excitation wavelength of 485 nm and a radiation wavelength of 523 nm.

Figure 10:
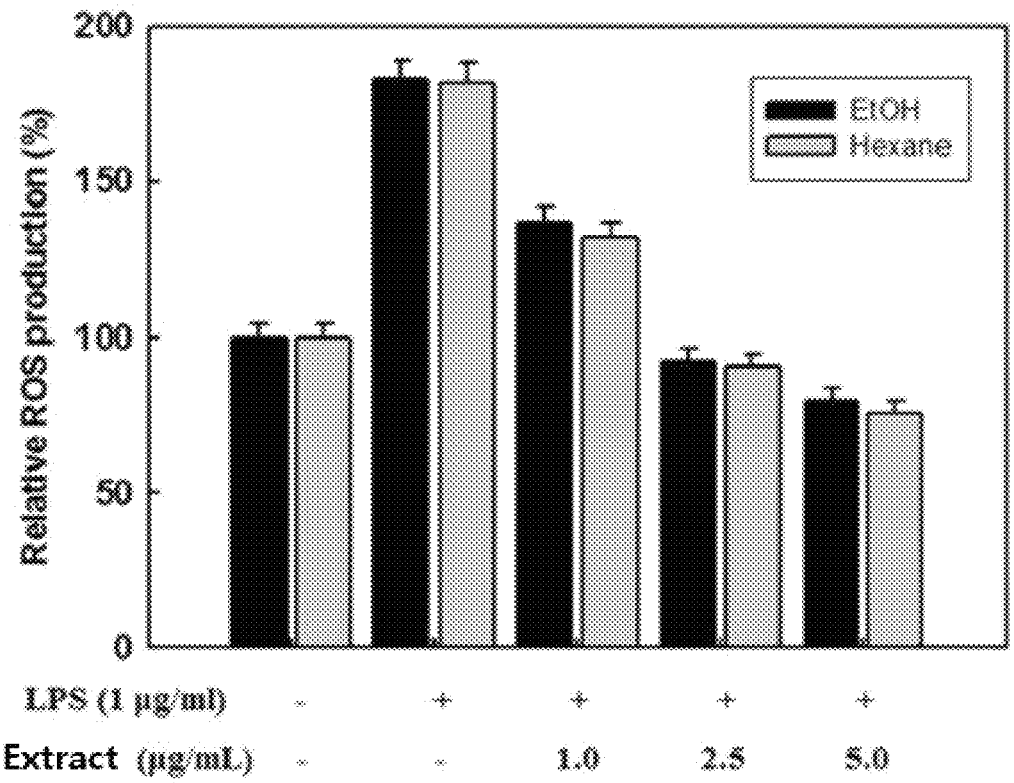
FIG. 10 illustrates the results of measuring LPS-induced reactive oxygen species (ROS) in macrophages according to treatment concentration of a *Sargassum serratifolium* ethanol extract and hexane fraction thereof of the present invention.

As illustrated in FIG. 10, the results indicate that the production of reactive oxygen species induced by lipopolysaccharide (LPS) was decreased treatment-concentration dependently in the experimental group treated with a *Sargassum serratifolium* ethanol extract and a hexane fraction thereof in macrophages, respectively. The $IC_{50}$ values of the ethanol extract and hexane fraction were 0.92±0.09 μg/mL and 0.88±0.08 μg/mL, respectively.

<2-3> Measurement of Antioxidative Activity by DPPH Method

The DPPH method (Blois, M. S.: Antioxidant determination by the use of a stable free radical, Nature, 26, 1199-1200, 1958) was used to measure the antioxidant effect of *Sargassum serratifolium* in vitro. The DPPH (1,1-diphenyl picrylhydrazyl) method is a method of measuring the antioxidative effect by hydrogen donating ability according to the degree of discoloration of deep purple color by reduction due to a physiologically active substance having an antioxidative activity such as tocopherol, ascorbate, flavonoid compounds, aromatic amines, Maillard-type browning agent, and peptide. For the measurement, 100 μl DPPH having a concentration of 200 μM and 100 μl the sample were mixed in a 96-well plate, and they reacted at room temperature for about 30 minutes. Then, the absorbance thereof was measured at 517 nm using a microplate reader. BHT was used as a positive control. The concentration was compared at the same as that of the sample.

DPPH radical scavenging activity was calculated by the method as described below.

Radical scavenging activity (%)=$(A_{DPPH}-A_{sample})/A_{DPPH} \times 100$

As shown in Table 1, the results indicate that $IC_{50}$ values of *Sargassum serratifolium* ethanol extract and hexane fraction thereof were 11.17±0.42 μg/mL and 9.05±0.21 μg/mL, respectively, and these values were lower than those of BHT used as a positive control (See Table 1).

<2-4> ABTs Assay

The ABTs assay is similar to the DPPH assay but differs in that antioxidative activity is measured by generating free radicals through chemical reactions. ABTs are reacted with potassium persulfate to generate ABTs anion radicals, which react with H-donors such as phenolic compounds to be converted to colorless ABTs. Accordingly, the degree of antioxidative activity may be determined by measuring the amount of ABTs consumed by reacting with a sample containing a phenolic compound.

ABTs antioxidative activity was measured by partially modified Van den Berg (1999) and others using the discoloration of ABTs radical-specific green color by antioxidants.

Potassium persulfate was added to 7 mM ABTs solution at a final concentration of 2.4 mM. They reacted in the dark for 12 hours to 16 hours at R/T so as to produce ABTs cations. The resulting ABTs cation was diluted to be used, having an absorbance value of 0.7±0.02. 10 μL the sample was treated with 190 μL ABTs+ working solution and reacted for 6 minutes in a 96-well plate. The absorbance thereof was measured at 732 nm. The radical scavenging activity was calculated from the measured values as follows. BHT was used as a positive control. The antioxidant ability of the sample is determined by the $IC_{50}$ value in which 50% of ABTs was reduced.

Percentage inhibiting activity I(%)=$(A_{control}-A_{sample})/A_{control} \times 100$ $A_{control}$: Control (blank sample)
$A_{control}$: Sample measurement value As shown in Table 1, the results indicate that $IC_{50}$ values of *Sargassum serratifolium* ethanol extract and hexane fraction thereof were 17.44±3.1 μg/mL and 14.69±3.4 μg/mL, respectively, and these values were somewhat higher than those of BHT used as a positive control (See Table 1).

<2-5> Hydroxyl Radical Scavenging

Hydroxyl radicals (—OH) are the most reactive radicals among oxygen radicals, which occur during aerobic metabolism in the human body. These radicals damage peripheral cells to create collateral living body molecules. A deoxyribose test was performed so as to measure the ability to scavenge hydroxyl radicals. Hydroxyl radicals attack deoxyribose to create small fragments. Some of which are pink when added with TBA (thiobarbituric acid) under an acidic pH environment, so the degree of damage by hydroxyl radicals is measured by absorbance at 532 nm.

Experimental methods described in Chandini, Ganesan, and Bhaskar (Chandini, S. K., Ganesan, p., and Bhaskar, N. (2008) In vitro antioxidant activities of three selected brown seaweeds of India. Food Chemistry, 107, 707-713) were modified to be used. This reaction used 20 mM phosphate buffer (pH 7.4). Ferric chloride ($FeCl_3$) and EDTA (ethylenediaminetetraacetic acid), respectively, were dissolved as to be 1 mM, and deoxyribose, a reaction substrate, was added to be 2.8 mM, thereby preparing a working solution. 1 ml the sample to be measured was mixed with the working solution, and 0.1 ml ascorbic acid (1 mM) is added to form Fe2+–EDTA mixture which is an oxidized form of ferric chloride ($FeCl_3$) and ethylenediamine tetraacetic acid (EDTA). Then, 0.5 ml of 20 mM hydrogen peroxide ($H_2O_2$) was added to form Fe3+–EDTA and HO radical. They were then incubated at 37° C. for 1 hour. After the incubation, 1 ml of 2.8% Trichloroacetic acid (TCA) and 1% TBA, respectively, were added. The mixture was boiled in boiling water at 100° C. for 30 minutes. The absorbance thereof was measured. BHT (2 μg/ml to 25 μg/ml) was used as a positive control.

Hydroxy radical scavenging ability (%)=$(A_{control}-A_{sample})/A_{control} \times 100$ $A_{control}$: Control (blank sample)
$A_{control}$: Sample measurement value As shown in Table 1, the results indicate that $IC_{50}$ values of *Sargassum serratifolium* ethanol extract and hexane fraction thereof were 1.12±0.15 μg/mL and 1.08±0.19 μg/mL, respectively. These values indicate that the antioxidative activity thereof was showed at a lower concentration compared to BHT used as a positive control (See Table 1).

TABLE 1

Antioxidant activity of *Sargassum serratifolium*
ethanol extract and hexane fraction thereof

|  | DPPH ($IC_{50}$, μg/ml) | ABTs ($IC_{50}$, μg/ml) | OH radical ($IC_{50}$, μg/ml) |
|---|---|---|---|
| *Sargassum serratifolium* | 11.17 ± 0.42 | 17.44 ± 3.1 | 1.12 ± 0.15 |
| Hexane fraction of *Sargassum serratifolium* | 9.05 ± 0.21 | 14.69 ± 3.4 | 1.08 ± 0.19 |
| BHT (Control) | 11.18 ± 0.15 | 7.77 ± 0.74 | 1.675 ± 0.21 |

Experimental Example 3

Evaluation of Cytotoxicity of *Sargassum serratifolium* Ethanol Extract and Compounds Separated Therefrom (Sargahydroquinoic Acid (SHO), Sargachromenol (SCM) and Sargaquinoic Acid (SOA)) of the Present Invention on 661W Photoreceptor Cells In this experiment, the cytotoxicity of *Sargassum serratifolium* ethanol extract and the compounds separated therefrom prepared in Examples 1 and 2 on 661W photoreceptor cells was confirmed. The 661W photoreceptor cells are cell lines established by Dr. Al-Ubaidi. Dr. Al-Ubaidi supplied the cells, which were used in the experiment.

661W photoreceptor cells were cultured in 96-wells at a concentration of $3 \times 10^3$ cells/well. Then, they were treated with 1.0 μg/ml *Sargassum serratifolium* ethanol extract or compounds separated therefrom (sargahydroquinoic acid (SHQ), sargachromenol (SCM), and sargaquinoic acid (SQA)) at a concentration of 1.0 μM and cultured for 24 hours. Then, the medium was replaced with medium containing MTS reagent. Then, they were cultured for 1 hour. Cell viability was measured by measuring the absorbance at 490 nm and comparing the results. The cell viability thereof was analyzed by Celltiter$^{96}$ Aqueous One solution assay kit (Promega).

Figure 11:
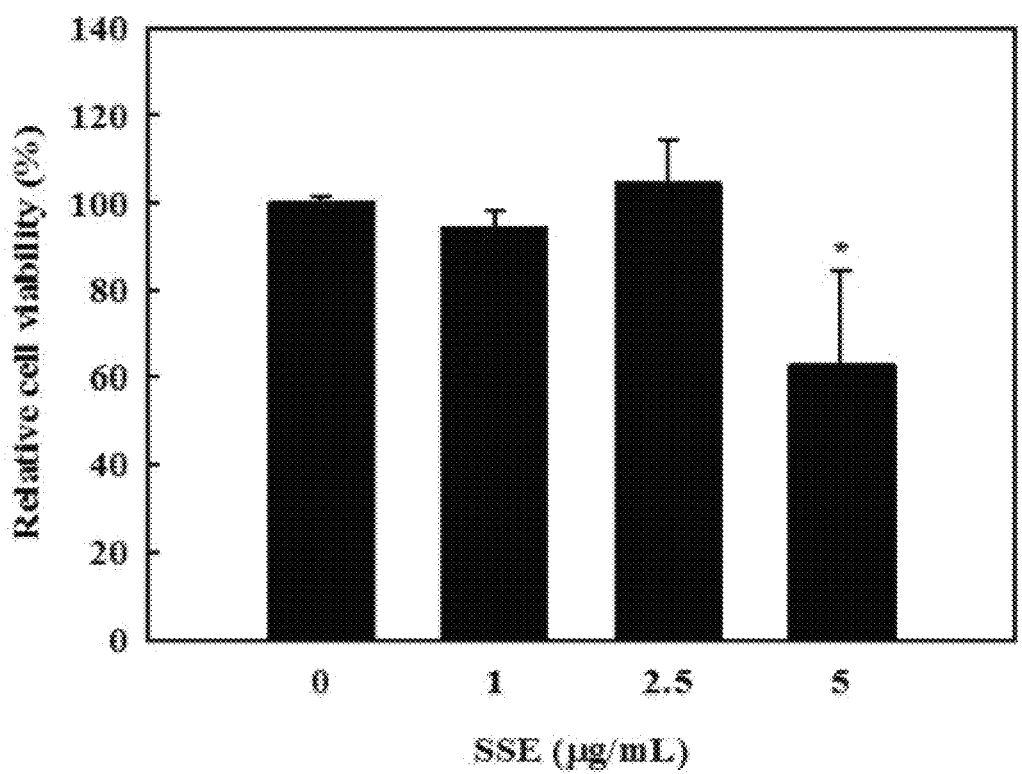
FIG. 11 illustrates the results of measuring the cytotoxicity of 661W, photoreceptor cells according to treatment with a *Sargassum serratifolium* ethanol extract (hereinafter, simply abbreviated as "SSE") of the present invention.
Figure 12:
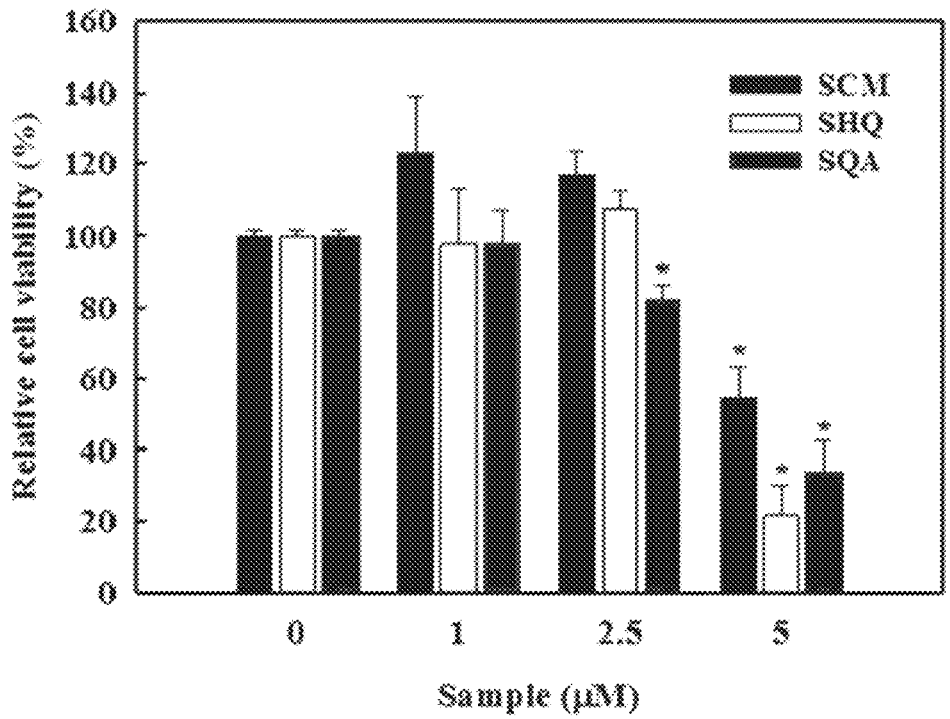
FIG. 12 illustrates the results of measuring the cytotoxicity of 661W, photoreceptor cells according to treatment with a compound selected from SSE ((sargahydroquinoic acid (hereinafter, simply abbreviated as "SHQ"), sargaquinoic acid (hereinafter, simply abbreviated as "SQA") or sargachromenol (hereinafter simply abbreviated as "SCM")).

As illustrated in FIGS. 11 and 12, the results indicate that no cytotoxicity was observed in the 661W photoreceptor cells in both *Sargassum serratifolium* ethanol extract (1 μg/ml) and the compound separated therefrom (1 μM). For reference, there was no cytotoxicity of *Sargassum serratifolium* ethanol extract up to a concentration of 2 μg/ml. There were also no cytotoxicity of sargahydroquinoic acid up to a concentration of 2.5 μM, sargachromenol up to a concentration of 2.5 μM, and sargaquinoic acid up to a concentration of 1.0 μM.

Experimental Example 4

Protective Effect of *Sargassum serratifolium* Ethanol Extract and Compounds Separated Therefrom (Sargahydroquinoic Acid (SHO), Sargachromenol (SCM) and Sargaquinoic Acid (SOA)) of the Present Invention on 661W Photoreceptor Cells from Oxidative Stress <4-1> Effect on the Cell Viability of 661W Cells Under Oxidative Stress In order to examine the protective effect of the *Sargassum serratifolium* ethanol extract and the compounds separated therefrom of the present invention prepared from Examples 1 and 2 on 661W photoreceptor cells, it is examined how the *Sargassum serratifolium* ethanol extract and the compounds separated therefrom of the present invention effect on the death of 661W photoreceptor cells treated with atRAL.

In other words, the atRAL is an intermediate metabolite of the visual cycle and is an aldehyde-type compound. The atRAL may induce excessive oxidative stress in cells. Therefore, when 661W photoreceptor cells were treated with the atRAL compound to induce the oxidative stress, the protective effect of the *Sargassum serratifolium* ethanol extract and the compound separated therefrom of the present invention on 661W photoreceptor cells was examined.

In detail, 661W photoreceptor cells were cultured in 96-wells at a concentration of $3 \times 10^3$ cells/well and treated with atRAL having a concentration of 1.8 μM (Sigma Aldrich, St. Louis, Mo., USA) for 24 hours. Then, the medium was replaced with medium containing MTS reagent, and they were cultured for 1 hour. The absorbance thereof was measured at 490 nm, and the results were compared to determine cell viability. The cell viability thereof was measured by Celltiter$^{96}$ Aqueous One solution assay kit (Promega).

Figure 13:
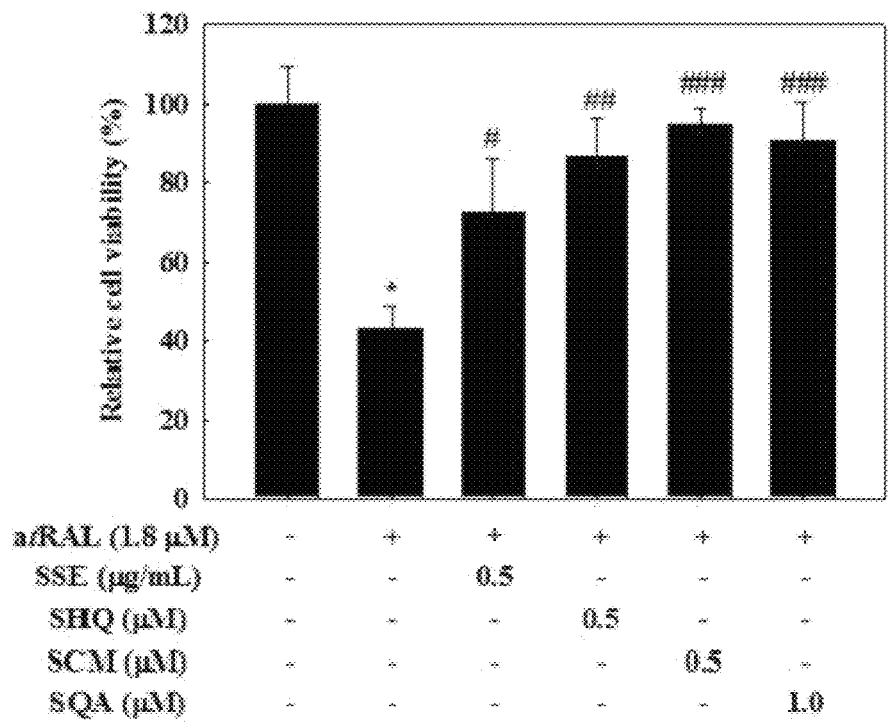
FIG. 13 illustrates the results of measuring cell viability of 661W cells according to the combined treatment of 661W photoreceptor cells derived from mice with an atRAL compound as oxidative stress inducer, a *Sargassum serratifolium* ethanol extract (SSE) and compounds separated therefrom of the present invention (SHQ, SCM, SQA), respectively. *P<0.05 refers to significance for non-treatment, and #P<0.05, ##P<0.01 and ###P<0.001 refer to significance for atRAL treatment.

As illustrated in FIG. 13, the results indicate that the cell viability of 661W photoreceptor cells was reduced by about 55% in the only atRAL-treated group, whereas the cell viability in the experimental group treated with 0.5 μg/mL *Sargassum serratifolium* ethanol extract and atRAL was increased by about 25% compared to the experimental group treated with the only atRAL.

Further, the cell viability of 661W photoreceptor cells was more than 90% in the experimental group treated with 0.5 μM of sargahydroquinoic acid (SHQ), sargachromenol (SCM) and sargaquinoic acid (SQA), respectively, so that no significant difference was found between the atRAL-treated group and the untreated group. The results demonstrate that the compounds derived from *Sargassum serratifolium* of the present invention have a very high protection effect on 661W photoreceptor cells.

In sum, it was concluded that the *Sargassum serratifolium* ethanol extract and the compounds separated therefrom of the present invention had the effect of protecting the photoreceptor cells within the range of showing no cytotoxicity.

<4-2> Inhibitory Effect on Reactive Oxygen Species in 661W Cells Under Oxidative Stress In order to check whether the *Sargassum serratifolium* ethanol extract and the compounds separated therefrom of the present invention prepared from Examples 1 and 2 have the antioxidant activity in 661W photoreceptor cells under oxidative stress, the inhibitory effect of the reactive oxygen species in 661W photoreceptor cells treated with atRAL was observed in this experiment.

For reference, 2',7'-dichlorodihydrofluorescein diacetate (DCFH-DA) converts to DCF, which expresses fluorescence in response to oxidative stress in cells. Therefore, the expression of DCF in cells is used as an indicator of the degree of oxidative stress.

In order to examine the antioxidative effect of the *Sargassum serratifolium* ethanol extract and the compounds separated therefrom of the present invention, atRAL (1.8 μM) and *Sargassum serratifolium* ethanol extract (0.5 μg/mL), sargachromenol (0.5 μM), sargahydroquinoic acid (0.5 μM), or sargaquinoic acid (1.0 μM) were added to medium mixed with DCFH-DA (20 μM), and the photoreceptor cells were treated with them and cultured for 30 minutes. Then, the cells were washed with PBS, and the cells were recovered. The cells expressing the fluorescence were measured using flow cytometry.

Figure 14:
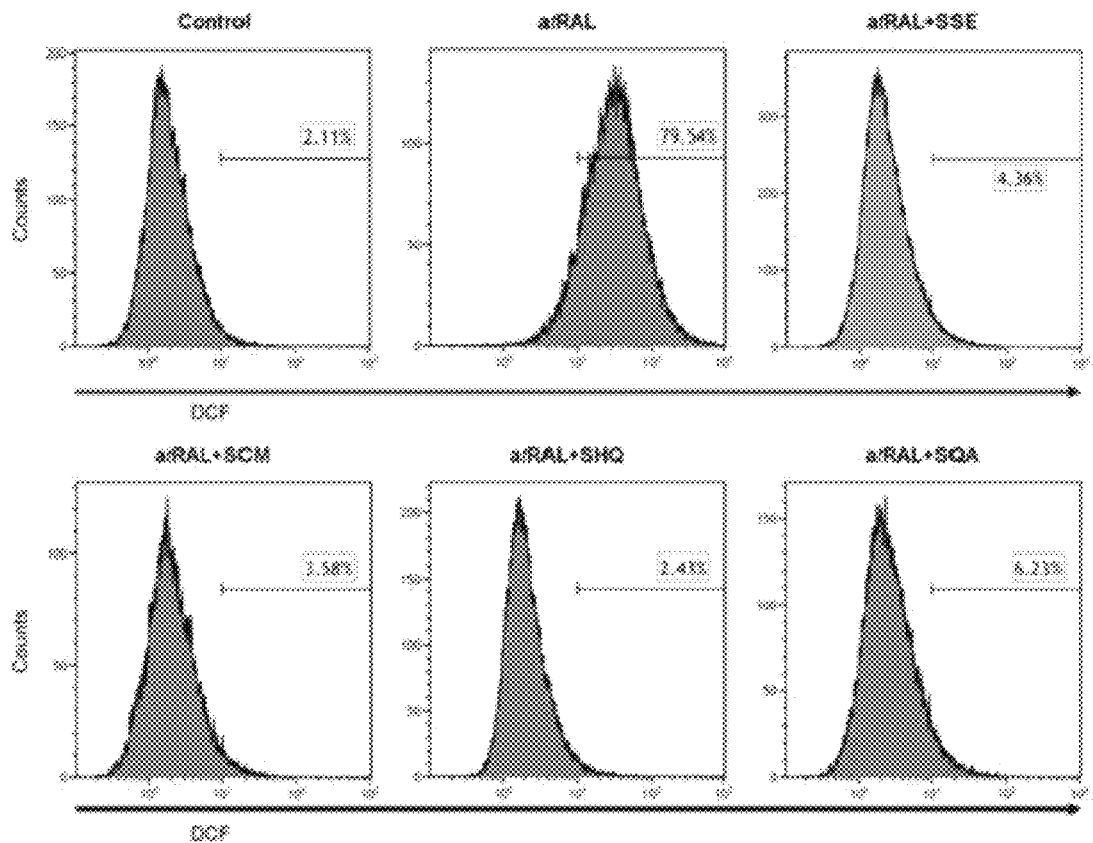
FIG. 14 illustrates the results of measuring the inhibitory level of reactive oxygen species production according to the combined treatment of 661W photoreceptor cells derived from mice with an atRAL compound as oxidative stress inducer, a *Sargassum serratifolium* ethanol extract (SSE) and compounds separated therefrom of the present invention (SHQ, SCM, SQA), respectively.

As illustrated in FIG. 14, the results demonstrate that the cells treated with atRAL only had a fluorescence expression level having about 80% higher than that of the control group. In the group treated with atRAL and *Sargassum serratifolium* ethanol extract 0.5 μg/mL, the fluorescence expression level was reduced by about 75% compared to the group treated with atRAL only. In the groups treated with atRAL and sargachromenol (0.5 μM), sargahydroquinoic acid (0.5 μM), or sargaquinoic acid (1.0 μM), the fluorescence expression levels were reduced by 76%, 77%, and 73%, respectively, and there was no difference from the control group untreated with atRAL.

Therefore, the *Sargassum serratifolium* ethanol extract and the compound separated therefrom were found to effectively inhibit atRAL-induced oxidative stress, thereby protecting photoreceptors.

<4-3> Inhibitory Effect on Malondialdehyde in 661W Cells Under Oxidative Stress

In order to check whether the *Sargassum serratifolium* ethanol extract and the compounds separated therefrom of the present invention prepared in Examples 1 and 2 have antioxidant activity in 661W photoreceptor cells under oxidative stress, the inhibitory level of malondialdehyde (MDA) production in 661W photoreceptor cells treated with atRAL was observed in this experiment. For reference, the malondialdehyde (MDA) is the result of lipid peroxidation by excessive oxidative stress in cells, and thus the amount of MDA in cells is a factor to measure the degree of oxidative stress.

In detail, samples of each of *Sargassum serratifolium* ethanol extract and the compounds separated therefrom were mixed with a specific amount of atRAL (1.8 μM) and *Sargassum serratifolium* ethanol extract (0.5 μg/mL), sargachromenol (0.5 μM), sargahydroquinoic acid (0.5 μM), or sargaquinoic acid (1.0 μM). The photoreceptor cells were treated with mixtures thereof. Then, they were cultured for 2 hours. The cells were then washed with PBS and the intracellular proteins were recovered. The number of proteins denatured by the lipid peroxides in cells was analyzed by protein immunoassay using MDA immunoblot kit (Cell biolabs).

Figure 15:
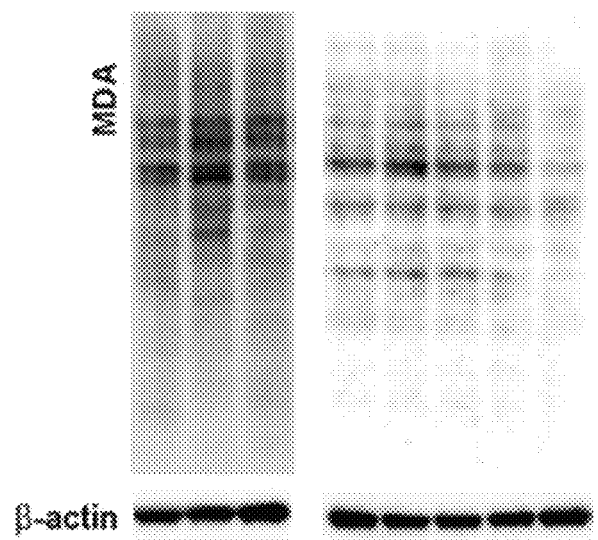
FIG. 15 illustrates the results of the protein immunoassay on an amount of malondialdehyde (MDA) protein in cells according to the combined treatment of 661W photoreceptor cells derived from mice with an atRAL compound as oxidative stress inducer, a *Sargassum serratifolium* ethanol extract (SSE) and compounds separated therefrom of the present invention (SHQ, SCM, SQA), respectively.

As illustrated in FIG. 15, the results indicate that the cells treated with atRAL only showed an increase in expression level of protein denatured by MDA compared with the control, whereas the group treated with atRAL and *Sargassum serratifolium* ethanol extract having 0.5 μg/mL of the present invention has decreased expression level of MDA peroxidase protein compared with the group treated with atRAL only. The expression level of MDA peroxidase protein was similarly decreased in the experimental groups treated with atRAL and the compounds separated from *Sargassum serratifolium* ethanol extract, respectively.

Therefore, it is determined that the *Sargassum serratifolium* ethanol extract and the compound separated therefrom effectively inhibit atRAL-induced oxidative stress so that the photoreceptors are protected by inhibiting peroxidation of cell membrane lipid component.

MODES OF THE INVENTION

The present invention is characterized by providing an antioxidant composition including a *Sargassum serratifolium* extract or a fraction thereof in an active ingredient.

"*Sargassum serratifolium*" of the present invention is a marine algae in Sargassaceae family of phaeophyta division, which is distributed in the south coast and Jeju region in Korea. The plant is 1 m to 4 m and its root diameter is 4 cm to 5 cm, which has cone-shape. It is like rubber and has a ring.

Until now, no study has been reported that such *Sargassum serratifolium* is related to the antioxidative activity.

The present inventors have selected the *Sargassum* belonging to *Sargassum* family as a substance of medicines, food, and cosmetic composition and produced extracts thereof. It is confirmed that *Sargassum serratifolium* among various kinds of Sargassum has an excellent antioxidative activity.

In detail, in order to evaluate the antioxidative activity of the *Sargassum serratifolium* ethanol extract and the hexane fraction separated therefrom, the present inventor measured the amount of nitric oxide produced in the following Experimental Example <2-1>. The results indicate that the production of nitric oxide (NO) induced by lipopolysaccharide (LPS) was decreased treatment-concentration dependently. The $EC_{50}$ values of the ethanol extract and the hexane fraction were 0.72 μg/mL and 0.68 μg/mL, respectively (See FIG. 9).

Further, in the following experimental example <2-2>, intracellular reactive oxygen species were measured. The results indicate that the production of reactive oxygen species induced by lipopolysaccharide (LPS) was decreased treatment-concentration dependently. The $IC_{50}$ values of the ethanol extract and the hexane fraction were 1.4±0.11 μg/mL and 1.3±0.12 μg/mL, respectively (See FIG. 10).

Further, DPPH radical scavenging activity, ABTs cation scavenging activity, and hydroxyl radical (—OH) scavenging activity were measured in the following Experimental Examples <2-3> to <2-5>, respectively. The results demonstrate that the *Sargassum serratifolium* ethanol extract and the hexane fraction thereof of the present invention showed 50% scavenging activity ($IC_{50}$) in the concentration range of 1 μg/ml to 20 μg/ml. These values show a higher antioxidative activity compared with BHT as a positive control group (See Table 1).

The results objectively demonstrate that the *Sargassum serratifolium* extract and the fraction thereof of the present invention show an excellent antioxidative activity, and it is supported by the experiments.

Therefore, the composition of the present invention, including *Sargassum serratifolium* extract and fraction thereof as an active ingredient may be useful as a functional material showing an antioxidative activity.

The *Sargassum serratifolium* extract according to the present invention may be used as one obtained by extracting and separating from nature using an extraction and separation method known in the art. The "extract" defined in the present invention may be extracted from *Sargassum serratifolium* using an appropriate solvent. It includes, for example, a crude extract, polar solvent extract or non-polar solvent extract of *Sargassum serratifolium*

Any pharmaceutically acceptable organic solvent may be used as an appropriate solvent for extracting the extract from the *Sargassum serratifolium*. Water or an organic solvent may be used. Various solvents such as purified water, alcohols having 1 to 4 carbon atoms such as methanol, ethanol, propanol, isopropanol, and butanol, acetone, ether, benzene, chloroform, ethyl acetate, methylene chloride, hexane, and cyclohexane may be used alone or in combination, but the solvent may not be limited thereto. Preferably, ethanol may be used, and more preferably, 95% ethanol may be used.

The extraction method may use any one selected from methods including hot water extraction, chilling extraction, reflux cooling extraction, solvent extraction, steam distillation, ultrasonic extraction, elution, pressing, and the like. Further, the desired extract may additionally perform a general fraction process and be purified using a general purification method. The method of preparing the *Sargassum serratifolium* extract of the present invention is not limited and may use any known method.

For example, in the *Sargassum serratifolium* extract included in the composition of the present invention, a primary extract extracted by the hot water extraction or solvent extraction may be prepared in a powder state by an additional process such as vacuum distillation and freeze-drying, or spray-drying. Further, the primary extract may obtain additionally purified fractions using various types of chromatography such as silica gel column chromatography, thin layer chromatography, high performance liquid chromatography, and the like.

Accordingly, in the present invention, the *Sargassum serratifolium* extract is a concept including all of the extracts, fractioned and purified materials, their dilutions, concentrates, or dried materials which are obtained in each step of extraction, fraction, or purification.

The method of preparing the *Sargassum serratifolium* extract according to the exemplary embodiment of the present invention is described below in more detail.

The dried *Sargassum serratifolium* is powdered. Then, 95% ethanol is used as an extraction solvent to perform the extraction using the reflux cooling extraction, followed by filtration and concentration.

This *Sargassum serratifolium* ethanol extract can be further fractionated using an n-hexane solvent. For example, the *Sargassum serratifolium* ethanol extract is dissolved in a mixed solvent of water and ethanol in a volume ratio of 9:1, and then equilibrated by adding the same amount of n-hexane. Then, the upper n-hexane soluble portion may be filtered and concentrated to produce the hexane fraction of *Sargassum serratifolium* ethanol extract.

Accordingly, the composition of the present invention corresponds to an antioxidant composition including the *Sargassum serratifolium* extract or the fraction thereof as an active ingredient.

In the present invention, "antioxidant composition" refers to a substance that prevents oxidation by inhibiting or eliminating active oxygen having an unstable state of oxygen.

The antioxidant composition of the present invention may be used for various objects and purposes requiring antioxidative activity. Specifically, the antioxidant composition may be used as a functional material which provides the antioxidative activity products which are applicable to various industrial fields such as pharmaceuticals, cosmetics, foods, and animal feed. It can also be used as a substance such as medicine preservative, a cosmetic preservative, a food preservative, a pharmaceutical additive, a cosmetic additive, a food additive, and a feed additive.

Hereinafter, pharmaceuticals, cosmetics, food, and animal feeds to which the antioxidant composition of the present invention can be applied are described in detail.

The antioxidant composition of the present invention may be a pharmaceutical composition for preventing or treating oxidation-related diseases, including a *Sargassum serratifolium* extract or a fraction thereof as an active ingredient.

The pharmaceutical composition of the present invention may be prepared by using pharmaceutically-suitable and physiologically-acceptable additives in addition to the active ingredient, and the additives may be an excipient, a disintegrant, a sweetener, a binder, a coating agent, an inflating agent, a glidant, a lubricant, a flavoring agent, and the like.

The pharmaceutical composition may preferably be formulated as a pharmaceutical composition by additionally including at least one of pharmaceutically acceptable carriers in addition to the active ingredient for administration.

A formulation of the pharmaceutical composition may be granules, powders, tablets, coated tablets, capsules, suppository, liquid, syrup, juice, a suspension, an emulsion, an ointment, an injectable liquid formulation, and the like.

For example, an active ingredient may be combined with an oral and non-toxic pharmaceutical acceptable inert carrier, such as ethanol, glycerol, water in order to formulate as a type of tablets or capsules. In addition, if it is necessary or required, a suitable binding agent, a lubricant, a disintegrant and a coloring agent may be also included as a mixture. The suitable binding agent includes starch, gelatin, natural sugars such as glucose or beta-lactose, corn sweetening agents, natural or synthetic gums such as acacia, tragacanth, or sodium oleate, sodium stearate, magnesium stearate, sodium benzoate, sodium acetate, sodium chloride, and the like, but is not limited thereto. The disintegrant includes starch, methylcellulose, agar, bentonite, xanthan gum, and the like, but is not limited thereto. A pharmaceutically acceptable carrier for a composition formulated as a liquid solution may be suitable for a sterilization and a body, and may be saline solution, sterilized water, Ringer solution, butter saline solution, albumin injection solution, dextrose solution, malto dextrin solution, glycerol, ethanol, and the mixture of at least one thereof, and other general additives, such as antioxidants, a buffering solution, and bacteriostat may be added as needed. In addition, tablets, granules, capsules, a pill, a dosage form for injecting, such as an aqueous solution, suspension, and an emulsion may be formulated by additionally adding a diluent, a dispersing agent, a surfactant, a binding agent, and a lubricant. Furthermore, it may be preferably formulated depending on each disease or each component using the method as disclosed in Remington's Pharmaceutical Science, Mack Publishing Company, Easton Pa. as a suitable method in the related art.

In an aspect of the present invention, the *Sargassum serratifolium* extract or fraction thereof of the present invention may be included in 0.00001% by weight to 40% by weight with respect to the total weight of the composition.

In another aspect of the present invention, the *Sargassum serratifolium* extract or fraction thereof of the present invention may be included at a concentration of 0.1 µg/ml to 10000 µg/ml with respect to the composition.

The oxidation-related diseases in which the pharmaceutical composition of the present invention may have a therapeutic effect may include nasitis, asthma, acute pain, chronic pain, paradentitis, gingivitis, inflammatory bowel disease, gout, myocardial infarction, arteriosclerosis, congestive heart failure, hypertension, angina pectoris, stomach ulcer, Alzheimer's disease, cerebral infarction, Down's syndrome, multiple sclerosis, obesity, diabetes, dementia, depression, schizophrenia, tuberculosis, sleep disorder, sepsis, a burn, pancreatitis, and eye diseases, but is not limited thereto.

The composition of the present invention may also be a food composition. Such a food composition may include various flavors or natural carbohydrates as well as the *Sargassum serratifolium* extract or fraction thereof as an active ingredient like conventional food compositions.

Examples of the natural carbohydrates include monosaccharides such as glucose and fructose; disaccharides such as maltose and sucrose; and polysaccharides such as general sugar including dextrin and cyclodextrin and sugar alcohols such as xylitol, sorbitol and erythritol. Natural flavors (thaumatin), stevia extract (e.g., rebaudioside A, glycyrrhizin, etc.) and synthetic flavors (e.g., saccharin, aspartame, etc.) may be advantageously used as a flavor.

The food composition of the present invention may be formulated in the same method as the pharmaceutical composition. So, the food composition may be used as a functional food or in by adding to various foods. Examples of foods to which the composition of the present invention may be added include beverages, meat, chocolates, foods, snack, pizza, ramen, other noodles, gums, candy, ice cream, alcoholic beverages, vitamin complexes, and health supplement foods.

Further, the food composition may include various nutrients, vitamins, minerals (electrolytes), flavors such as synthetic flavors and natural flavors, coloring agents and enhancers (cheese, chocolate, etc.), pectic acid and its salts, alginic acid and its salts, organic acids, protective colloid thickeners, pH adjusting agents, stabilizers, preservatives, glycerin, alcohols, carbonating agents used in carbonated beverages, and the like as well as the *Sargassum serratifolium* extract and fraction thereof as an active ingredient. In addition, the food composition of the present invention may include flesh for the production of natural fruit juices, fruit juice drinks, and vegetable drinks.

Such a *Sargassum serratifolium* extract or a fraction thereof, which is the active ingredient of the present invention, is a natural material and has few side effects, unlike chemicals, so that it can be safely used for long-term use for the purpose of imparting antioxidant function.

The present invention may include a health functional food for preventing or alleviating oxidation-related diseases, in which the health functional food may include a *Sargassum serratifolium* extract or a compound separated therefrom as an active ingredient.

The health functional food of the present invention may be produced and processed in the form of tablets, capsules, powders, granules, liquids, and pills for the purpose of preventing or alleviating oxidation-related diseases.

The term "health functional food" in the present invention refers to foods produced or processed using raw materials or components that have useful functionality in the human body according to the health functional food law or means that the food is ingested for the purpose of obtaining a beneficial effect for health use such as controlling nutrients or physiological action for the structure and function of the human body.

The health functional food of the present invention may include common food additives. The conformity of the "food additive" is determined, as long as there are no other regulations, in consideration with the standard and criteria of the corresponding item according to the general rule of the food additives codex and general tests approved by the Korean Ministry of Food and Drug Safety.

The items listed on the "food additives codex" include chemical compounds such as ketones, glycine, calcium citrate, nicotinic acid, and cinnamic acid; natural additives such as persimmon color, licorice extract, crystalline cellulose, kaoliang color, and guar gum; and mixed preparations such as L-glutamic acid sodium preparations, alkalis additives for noodle, preservative preparations, tar color preparations.

For example, in order to produce a health functional food in a tablet form, a mixture of the *Sargassum serratifolium* extract or fraction thereof as an active ingredient of the present invention, excipients, binders, disintegrants, and other additives can be granulated using a conventional method, and then compression molding process is performed with lubricants. Alternatively, the mixture can be directly subjected to the compression molding process. In addition, when needed, the health functional food in a tablet form may include sweetening agents.

Among health functional foods in a capsule form, a hard capsule formulation can be produced by filling a conventional hard capsule with a mixture of the *Sargassum serratifolium* extract or fraction thereof as an active ingredient of the present invention and additives such as excipients; and a soft capsule formulation can be produced by filling a capsule support of gelatin with a mixture of the *Sargassum serratifolium* extract or fraction thereof as an active ingredient of the present invention and additives such as excipients. When needed, the soft capsule formulation can include plasticizers, such as glycerin or sorbitol, coloring agents, and preservatives.

A health functional food in a pill form can be produced by molding a mixture of the *Sargassum serratifolium* extract or fraction thereof as an active ingredient of the present invention, excipients, binders, and disintegrants using well-known methods. When needed, the health functional food in a pill form can be coated with white sugar or other coating materials, or the surface thereof can be coated with starch, talc, or other materials.

A health functional food in a granule form can be produced by granulating a mixture of the *Sargassum serratifolium* extract or fraction thereof as an active ingredient of the present invention, excipients, binders, and disintegrants using well-known methods. When needed, the health functional food in a granule form can include flavoring agents and sweetening agents.

The health functional food containing the *Sargassum serratifolium* extract or the fraction thereof as an active ingredient of the present invention has been experimentally proved to have excellent antioxidative effects as shown in the following examples, and thus it is effective for preventing or alleviating oxidation-related diseases.

The health functional food may be beverages, meat, chocolates, foods, snack, pizza, ramen, other noodles, gums, candy, ice cream, alcoholic beverages, vitamin complexes, and health supplement foods.

The composition of the present invention may be a cosmetic composition as well as a pharmaceutical composition or a food composition.

The *Sargassum serratifolium* extract or fraction thereof of the present invention has an excellent scavenging activity against the most reactive hydroxyl radicals among the reactive oxygen species as well as scavenging activity against nitric oxide so that it has an excellent antioxidative activity. Thus, the composition including the *Sargassum serratifolium* extract or fraction thereof may be useful as a cosmetic composition because it is effective for skin protection and skin treatment from reactive oxygen species (ROS) that induce damage to human cells to accelerate aging and mediate oxidation-related diseases.

When the composition of the present invention is prepared as a cosmetic composition, the composition of the present invention may include not only the *Sargassum serratifolium* extract or fraction thereof, but also compositions commonly used in cosmetic compositions such as commonly used supplements such as antioxidants, stabilizers, solubilizers, vitamins, pigments and flavors, and carriers.

In addition, the composition of the present invention may be used in combination with the above-mentioned *Sargassum serratifolium* extract or fraction thereof and conventionally used antioxidants to the extent that it does not adversely affect the skin protecting effect by reacting with the *Sargassum serratifolium* extract or fraction thereof.

Examples of products added to the cosmetic composition of the present invention may include cosmetics such as astringents, toners, nutritional lotions, various creams, essences, packs and foundations, cleansers, facial cleaning agents, soaps, treatment agents, and beauty liquids.

Specific formulations of the cosmetic compositions of the present invention include skin lotions, skin softeners, skin toners, astringents, lotions, milky lotions, moisturizing lotions, nutritional lotions, massage creams, nutritional creams, moisturizing creams, hand creams, essences, nutritional essences, packs, soap, shampoo, cleansing foams, cleansing lotions, cleansing creams, body lotions, body cleansers, milky liquid, lipsticks, makeup base, foundations, press powders, loose powders, eyeshadow, and the like.

According to a preferred embodiment of the present invention, the content of the *Sargassum serratifolium* extract or fraction thereof of the present invention is 0.00001% by weight to 40% by weight, preferably 0.1% by weight to 20% by weight, more preferably 1.0% by weight to 20% by weight with respect to the total weight of the composition. When the content of the *Sargassum serratifolium* extract or fraction thereof is less than 0.00001% by weight, the anti-oxidative effect caused by the extract and the fraction thereof is significantly reduced. When the content is more than 40% by weight, skin irritation may be caused and a problem may occur in the formulation thereof.

Meanwhile, the cosmetic composition according to the present invention can be formulated in which the *Sargassum serratifolium* extract or fraction thereof is contained inside the nanoliposome, resulting in its stabilization. When the extract (or fraction thereof) is contained inside the nanoliposome, the composition of the extract (or fraction thereof) is stabilized. Thus, when formulated, problems such as precipitation formation, discoloration, and changing scent may be solved. Further, the solubility and transdermal absorption rate thereof may be improved. Therefore, the expected efficacy from the extract (or fraction thereof) may be maximized.

In the present invention, nanoliposomes are liposomes having a typical liposome shape and refer to liposome having an average particle diameter of 10 nm to 500 nm. According to a preferred embodiment of the present invention, the average particle diameter of the nanoliposome is 50 nm to 300 nm. When the average particle diameter of the nanoliposome exceeds 300 nm, among technological effects to be achieved in the present invention, the improvement of the skin penetration thereof and the improvement of the formulation stability thereof are very weak.

The nanoliposomes used to stabilize the extract (or fraction thereof) according to the present invention may be prepared using a mixture including a polyol, an oily composition, a surfactant, a phospholipid, a fatty acid, and water.

The polyol used in the nanoliposome of the present invention is not particularly limited, but preferably includes at least one selected from the group consisting of propylene glycol, dipropylene glycol, 1,3-butylene glycol, glycerin, methylpropanediol, isopropylene glycol, pentylene glycol, erythritol, xylitol, sorbitol, and mixtures thereof. The content thereof is 10% by weight to 80% by weight, preferably 30% by weight to 70% by weight, with respect to the total weight of the nanoliposome.

The oil composition used in the preparation of the nanoliposome of the present invention may include a variety of oils known in the art and, but include preferably hydrocarbon-based oil such as hexadecane and paraffin oil, an ester-based synthetic oil, silicone oil such as dimethicone-based oil and cyclomethicone-based oil, animal-vegetable oil such as sunflower oil, corn oil, soybean oil, avocado oil, sesame oil and fish oil, ethoxylated alkyl ether-based oil, propoxylated alkyl ether-based oil, sphingoid lipid such as phytosphingosine, sphingosine and sphinganine, cerebroside cholesterol, sitosterol cholesteryl sulfate, cetostearyl sulfate, $C_{10-40}$ fatty alcohols and mixtures thereof. The amount thereof may be 1.0% by weight to 30.0% by weight, and preferably 3.0% by weight to 20.0% by weight with respect to the total weight of the nanoliposome.

Any surfactant known in the art may be used as the surfactant used in the preparation of the nanoliposome of the present invention. For example, anionic surfactants, cationic surfactants, amphoteric surfactants and nonionic surfactants may be used. Preferably, anionic surfactants and nonionic surfactants may be used. Specific examples of anionic surfactants include alkyl acyl glutamate, alkyl phosphates, alkyl lactylate, dialkyl phosphate and trialkyl phosphate. Specific examples of nonionic surfactants include alkoxylated alkyl ether, alkoxylated alkyl ester, alkyl polyglycoside, polyglyceryl ester and sugar ester. Particularly, the preferred surfactant is polysorbate-based compound belonging to nonionic surfactants. The amount thereof may be 0.1% by weight to 10% by weight, preferably 0.5% by weight to 5.0% by weight with respect to the total weight of the nanoliposome.

Another composition used in the preparation of the nanoliposome of the present invention is phospholipids which are amphiphilic lipids. The phospholipids include natural phospholipids (for example, egg yolk lecithin or soy lecithin, sphingomyelin) and synthetic phospholipids (for example, dipalmitoyl phosphatidylcholine or hydrogenated lecithin). Preferably, the phospholipid is lecithin. In particular, unsaturated lecithin or saturated lecithin derived from natural origin extracted from soybean or egg yolk is preferred. Typically, the amount of phosphatidylcholine in the naturally occurring lecithin is 23% to 95%, and the amount of phosphatidyl ethanolamine is 20% or less. In the preparation of the nanoliposome of the present invention, the amount of phospholipid to be used is 0.5% by weight to 20.0% by weight, preferably 2.0% by weight to 8.0% by weight with respect to the total weight of the nanoliposome.

The fatty acid used in the preparation of the nanoliposome of the present invention includes higher fatty acids, preferably saturated or unsaturated fatty acids of $C_{12-22}$ alkyl chains, such as lauric acid, myristic acid, palmitic acid, stearic acid, oleic acid, and linoleic acid. The amount thereof may be 0.05% by weight to 3.0% by weight, preferably 0.1% by weight to 1.0% by weight with respect to the total weight of the nanoliposome.

The water used in the preparation of the nanoliposome of the present invention is generally deionized distilled water. The amount thereof may be 5.0% by weight to 40% by weight with respect to the total weight of the nanoliposome.

The nanoliposome may be prepared by a variety of methods known in the art, but the most preferred method is carried out by applying a mixture including the components to a high-pressure homogenizer. The nanoliposome may be prepared by a high-pressure homogenizer under various conditions (for example, pressure, number of times, etc.) depending on the desired particle size. Preferably, the nanoliposome may be prepared in which the mixture passes through a high-pressure homogenizer 1 to 5 times at a pressure of 600 bar to 1200 bar.

The cosmetic composition according to the present invention may contain the *Sargassum serratifolium* extract or fraction thereof having 0.1% by weight to 20.0% by weight with respect to the weight of the nanoliposome and more preferably 1.0% by weight to 10.0% by weight for stabilizing the formulation.

In an aspect of the present invention, the *Sargassum serratifolium* extract or fraction thereof may be included in the cosmetic composition at a concentration of 0.1 µg/ml to 10000 µµg/ml.

Further, the composition of the present invention may be a feed composition or a feed additive which may impart the antioxidant functionality thereto.

The feed composition according to the present invention may contain the *Sargassum serratifolium* extract or fraction thereof in an amount of 0.1% by weight to 50% by weight, more preferably 1% by weight to 20% by weight with respect to the total weight of the composition, but is not limited thereto. Meanwhile, when used as a feed additive, the *Sargassum serratifolium* extract or fraction thereof can be mixed and used in the feed composition.

Further, the present invention provides an antioxidation or anti-aging method including administering a *Sargassum serratifolium* extract or a compound separated therefrom to an individual.

The antioxidation or anti-aging method of the present invention includes administering a *Sargassum serratifolium* extract or a compound separated therefrom of the present invention to an individual in a therapeutically effective amount. The specific therapeutically effective amount for any particular individual may vary depending on various factors well known in the medical art and other factors including the kind and degree of the response to be achieved, whether other agents are used therewith or not, specific composition, the patient's age, body weight, health conditions, gender, and diet, the time and route of administration, the secretion rate of the composition, the time period of therapy, other drugs used in combination or coincidentally with the specific composition. Therefore, the effective amount of the composition suitable for the purpose of the present invention is preferably determined in consideration of the matters as described above.

Any mammal is applicable to the individual. The mammal includes livestock such as cows, pigs, sheep, horses, dogs and cats as well as humans and primates.

Further, the present invention is characterized by providing an antioxidant composition for preventing or alleviating eye diseases, which includes the *Sargassum serratifolium* extract or a fraction thereof as an active ingredient.

Until now, the *Sargassum serratifolium* has not been reported to have the preventive, ameliorative and therapeutic effects on eye diseases.

The present inventors have confirmed through experiments that the *Sargassum serratifolium* has superior anti-oxidative activity among the various types of *Sargassum* so that it is effective in preventing, alleviating, and treating eye diseases associated with oxidative stress.

In detail, in order to examine preventive, ameliorative and therapeutic effects of the *Sargassum serratifolium* extract and compound separated therefrom (SHQ, SCM and SQA) on eye diseases, the present inventor investigated their effects on the survival rate of oxidative stressed 661W cells (mouse-derived photoreceptor cells) in the following Experimental Example 4-1. The results indicate that the group treated with the only atRAL, which is an oxidative stress inducer, showed the decreased survival rate of 661W photoreceptor cells by about 55%, on the other hand, the group treated with atRAL and the *Sargassum serratifolium* ethanol extract together exhibited the increased survival rate of 661W photoreceptor cells by about 25% compared with the group treated with the only atRAL. Further, the group treated with atRAL and SHQ, SCM and SQA, respectively, showed more than 90% of the survival rate of 661W photoreceptor cells, indicating no significant difference compared to the group non-treated with atRAL. The results demonstrate that the *Sargassum serratifolium* ethanol extract and the compound separated therefrom (SHQ, SCM and SQA) of the present invention have a very high protective effect on the 661W photoreceptor cells within the range of no cytotoxicity (See FIG. 13).

Further, in the following Experimental Example 4-2, the effect of inhibiting reactive oxygen species was examined in 661W photoreceptor cells treated with atRAL, which is an oxidative stress inducer. The results indicate that the group treated with atRAL and the *Sargassum serratifolium* ethanol extract together exhibited the deceased fluorescence expression level by about 75% compared with the group treated with the only atRAL. Further, the group treated with atRAL and SHQ, SCM and SQA, respectively, showed the decreased fluorescence expression level by about 76%, 77% and 73%, indicating no significant difference compared to the group non-treated with atRAL. Therefore, it was confirmed that the *Sargassum serratifolium* ethanol extract and the compound separated therefrom (SHQ, SCM and SQA) of the present invention effectively inhibit the oxidative stress induced by atRAL, thereby protecting photoreceptor cells (See FIG. 14).

Further, the inhibitory effect on malondialdehyde (MDA) in 661W cells under the oxidative stress was measured in the following Experimental Example 4-3. The results show that the expression level of protein denatured by MDA increased in the cells treated with the only atRAL. Meanwhile the expression level of MDA peroxidase protein in the experimental group treated with atRAL and the *Sargassum serratifolium* ethanol extract of the present invention together decreased compared to the group with the only atRAL. In addition, it was confirmed that the expression level of MDA peroxidase protein was effectively reduced in the group treated with atRAL and SHQ, SCM and SQA, respectively. Therefore, it was determined that the *Sargassum serratifolium* ethanol extract and the compound separated therefrom effectively inhibit the oxidative stress, thereby resulting in the inhibition of peroxidation of cell membrane lipid component so as to protect photoreceptor cells (See FIG. 15).

The results demonstrate objectively through experiments that the *Sargassum serratifolium* extract and compound separated therefrom of the present invention (SHQ, SCM and SQA) are excellent effective in preventing, alleviating, and treating eye diseases associated with oxidative stress.

Therefore, the composition of the present invention, including a *Sargassum serratifolium* extract and a compound separated therefrom as an active ingredient may be useful as a functional material for preventing, alleviating, and treating eye diseases associated with oxidative stress.

The *Sargassum serratifolium* extract according to the present invention may be used as one obtained by extracting and separating from nature using an extraction and separation method known in the art. The "extract" defined in the present invention may be extracted from *Sargassum serratifolium* using an appropriate solvent. It includes, for example, a crude extract, polar solvent extract or non-polar solvent extract of the *Sargassum serratifolium*.

Any pharmaceutically acceptable organic solvent may be used as an appropriate solvent for extracting the extract from the *Sargassum serratifolium*. Water or an organic solvent may be used. Various solvents such as purified water, alcohols having 1 to 4 carbon atoms such as methanol, ethanol, propanol, isopropanol and butanol, acetone, ether, benzene, chloroform, ethyl acetate, methylene chloride, hexane and cyclohexane may be used alone or in combination, but the solvent may not be limited thereto. Preferably, ethanol may be used, and more preferably, 95% ethanol may be used.

The extraction method may use any one selected from methods including hot water extraction, chilling extraction, reflux cooling extraction, solvent extraction, steam distillation, ultrasonic extraction, elution, pressing, and the like. Further, the desired extract may additionally perform a general fraction process and be purified using a general purification method. The method of preparing the *Sargassum serratifolium* extract of the present invention is not limited and may use any known method.

For example, in the *Sargassum serratifolium* extract included in the composition of the present invention, a primary extract extracted by the hot water extraction or solvent extraction may be prepared in a powder state by an additional process such as vacuum distillation and freeze-drying or spray-drying. Further, the primary extract may obtain additionally purified fractions using various types of chromatography such as silica gel column chromatography, thin layer chromatography, high performance liquid chromatography.

Accordingly, in the present invention, the *Sargassum serratifolium* extract is a concept including all of the extracts, fractioned and purified materials, their dilutions, concentrates, or dried materials which are obtained in each step of extraction, fraction, or purification.

The method of preparing the *Sargassum serratifolium* extract according to the exemplary embodiment of the present invention is described below in more detail.

The dried *Sargassum serratifolium* is powdered. Then, 95% ethanol is used as an extraction solvent to perform the extraction using the reflux cooling extraction, followed by filtration and concentration.

Further, SHQ, SCM and SQA compounds may be separated from the *Sargassum serratifolium* ethanol extract of the present invention through step-by-step processes (See Example 2).

Accordingly, the composition of the present invention corresponds to a pharmaceutical composition for preventing or treating eye diseases, which includes the *Sargassum serratifolium* extract or compound separated therefrom as an active ingredient.

In an aspect of the present invention, the *Sargassum serratifolium* extract may be a *Sargassum serratifolium* ethanol extract extracted with ethanol solvent, and the compound may be sargahydroquinoic acid (SHQ), sargaquinoic acid (SQA) or sagachromenol (SCM).

The pharmaceutical composition of the present invention may be prepared by using pharmaceutically-suitable and physiologically-acceptable additives in addition to the active ingredient, and the additives may be an excipient, a disintegrant, a sweetener, a binder, a coating agent, an inflating agent, a glidant, a lubricant, a flavoring agent, and the like.

The pharmaceutical composition may preferably be formulated as a pharmaceutical composition by additionally including at least one of pharmaceutically acceptable carriers in addition to the active ingredient for administration.

A formulation of the pharmaceutical composition may be granules, powders, tablets, coated tablets, capsules, suppository, liquid, syrup, juice, a suspension, an emulsion, an ointment, an injectable liquid formulation, and the like.

For example, an active ingredient may be combined with an oral and non-toxic pharmaceutical acceptable inert carrier, such as ethanol, glycerol, and water in order to formulate as a type of tablets or capsules. In addition, if it is necessary or required, a suitable binding agent, a lubricant, a disintegrant and a coloring agent may be also included in a mixture. The suitable binding agent includes starch, gelatin, natural sugars such as glucose or beta-lactose, corn sweetening agents, natural or synthetic gums such as acacia, tragacanth or sodium oleate, sodium stearate, magnesium stearate, sodium benzoate, sodium acetate, sodium chloride, and the like, but is not limited thereto. The disintegrant includes starch, methylcellulose, agar, bentonite, xanthan gum, and the like, but is not limited thereto. A pharmaceutically acceptable carrier for a composition formulated as a liquid solution may be suitable for a sterilization and a body, and may be saline solution, sterilized water, Ringer solution, butter saline solution, albumin injection solution, dextrose solution, malto dextrin solution, glycerol, ethanol, and the mixture of at least one thereof, and other general additives, such as antioxidants, a buffering solution, and bacteriostat may be added as needed. In addition, tablets, granules, capsules, a pill, a dosage form for injecting, such as an aqueous solution, suspension, and an emulsion may be formulated by additionally adding a diluent, a dispersing agent, a surfactant, a binding agent, and a lubricant. Furthermore, it may be preferably formulated depending on each disease or each component using the method as disclosed in Remington's Pharmaceutical Science, Mack Publishing Company, Easton Pa. as a suitable method in the related art.

In an aspect of the present invention, the *Sargassum serratifolium* extract or compound separated therefrom (SHQ, SCM and SQA) of the present invention may be included in 0.00001% by weight to 40% by weight with respect to the total weight of the composition.

In another aspect of the present invention, the *Sargassum serratifolium* extract or compound separated therefrom of the present invention may be included at a concentration of 0.1 µg/ml to 10000 µg/ml with respect to the composition, and the compound separated from the *Sargassum serratifolium* extract (SHQ, SCM, and SQA) may be included at a concentration of 0.1 µg/ml to 10000 µg/ml with respect to the food composition.

The eye diseases for which the pharmaceutical composition of the present invention has therapeutic effects include age-related macular degeneration, glaucoma, diabetic retinopathy, retinitis pigmentosa, choroidal neovascular membrane, uveitis, myopic degeneration, ocular tumor, central retinal vein occlusion, skin flushing, ocular neovascularization, central serous retinopathy, dry eye syndrome, central retinal artery occlusion, cystoid macular edema, and the like, but are not limited thereto.

In particular, the *Sargassum serratifolium* extract or compounds separated therefrom (SHQ, SCM, and SQA) of the present invention has the effect of protecting photoreceptor cells through an excellent antioxidative activity so that it may be more effective in treating the oxidative stress-related eye disease among eye diseases.

For reference, the oxidative stress plays a critical role in eye tissue and eye disease. The retina of the eye is the tissue with the fastest metabolic rate in the human body, thereby creating a tremendous amount of oxidative stress. Furthermore, when the eye is exposed to high-energy ultraviolet rays, the reactive oxygen species having high reactivity is generated in a significant amount, resulting in fatal eye damage.

The age-related macular degeneration (hereinafter, referred as to "AMD") is the most active subject among studies about eye diseases. The several causes of the disease include the production of reactive oxygen derivatives due to excessive oxygen use, accumulation of lipofuscin-retinoid derivatives (bisretinylethanolamine (A2E)), and oxidation by light, but the specific mechanism and treatment methods are not yet known (Zarbin, 2004, Arch Ophthalmol 122, 598-614; Kasahara et al., 2005, Invest Ophthalmol Vis Sci 46, 3426-3434).

Further, the recent research conducted by the department of ophthalmology of St. Mary's Hospital in Korea has revealed that hydrogen peroxide ($H_2O_2$) in the body induces destruction of the retinal pigment epithelium, resulting in macular degeneration.

Therefore, the material capable of inhibiting or alleviating oxidative stress in the eye tissues and cells may be effectively used for preventing or treating various eye diseases (especially, macular degeneration) caused by the oxidative stress.

Accordingly, the composition of the present invention includes the *Sargassum serratifolium* extract or compounds separated therefrom (SHQ, SCM and SQA) as an active ingredient. The active ingredient has the effect of protecting photoreceptor cells through an excellent antioxidative activity so that it may be useful for a pharmaceutical composition for preventing or treating eye diseases caused by the oxidative stress.

Further, the present invention provides a method of treating an eye disease, including administering a *Sargassum serratifolium* extract or a compound separated therefrom to an individual.

The method of treating an eye disease of the present invention includes administering a *Sargassum serratifolium* extract or a compound separated therefrom of the present invention to an individual in a therapeutically effective amount. The specific therapeutically effective amount for any particular individual may vary depending on various factors well known in the medical art and other factors including the kind and degree of the response to be achieved, whether other agents are used therewith or not, specific composition, the patient's age, body weight, health conditions, gender, and diet, the time and route of administration, the secretion rate of the composition, the time period of therapy, and other drugs used in combination or coincidentally with the specific composition. Therefore, the effective amount of the composition suitable for the purpose of the present invention is preferably determined in consideration of the matters as described above.

Any mammal is applicable to the individual. The mammal includes livestock such as cows, pigs, sheep, horses, dogs, and cats as well as humans and primates.

Further, the present invention provides a food composition for preventing or alleviating eye diseases, which includes a *Sargassum serratifolium* extract or a fraction thereof in an active ingredient.

In an aspect of the present invention, the *Sargassum serratifolium* extract may be a *Sargassum serratifolium* ethanol extract extracted with ethanol solvent, and the compound may be sargahydroquinoic acid (SHQ), sargaquinoic acid (SQA), or sagachromenol (SCM).

Such a food composition may include various flavors or natural carbohydrates as well as the *Sargassum serratifolium* extract or compound separated therefrom (SHQ, SCM and SQA) as an active ingredient like conventional food compositions.

Examples of the natural carbohydrates include monosaccharides such as glucose and fructose; disaccharides such as maltose and sucrose; and polysaccharides such as general sugar including dextrin and cyclodextrin and sugar alcohols such as xylitol, sorbitol, and erythritol. Natural flavors (thaumatin), stevia extract (e.g., rebaudioside A, glycyrrhizin, etc.), and synthetic flavors (e.g., saccharin, aspartame, etc.) may be advantageously used as a flavor.

The food composition of the present invention may be formulated in the same method as the pharmaceutical composition. So, the food composition may be used as a functional food or in by adding to various foods. Examples of foods to which the composition of the present invention may be added include beverages, meat, chocolates, foods, snack, pizza, ramen, other noodles, gums, candy, ice cream, alcoholic beverages, vitamin complexes, and health supplement foods.

Further, the food composition may include various nutrients, vitamins, minerals (electrolytes), flavors such as synthetic flavors and natural flavors, coloring agents and enhancers (cheese, chocolate, etc.), pectic acid and its salts, alginic acid and its salts, organic acids, protective colloid thickeners, pH adjusting agents, stabilizers, preservatives, glycerin, alcohols, carbonating agents used in carbonated beverages, and the like as well as the *Sargassum serratifolium* extract or compound separated therefrom (SHQ, SCM, and SQA) as an active ingredient. In addition, the food composition of the present invention may include flesh for the production of natural fruit juices, fruit juice drinks and vegetable drinks.

The eye diseases for which the food composition of the present invention has alleviative effects may be oxidative stress-related eye diseases, which include, for example, age-related macular degeneration, glaucoma, diabetic retinopathy, retinitis pigmentosa, choroidal neovascular membrane, uveitis, myopic degeneration, ocular tumor, central retinal vein occlusion, skin flushing, ocular neovascularization, central serous retinopathy, dry eye syndrome, central retinal artery occlusion, cystoid macular edema, and the like, but are not limited thereto.

In an aspect of the present invention, the *Sargassum serratifolium* extract or compound separated therefrom (SHQ, SCM and SQA) of the present invention may be included in 0.00001% by weight to 40% by weight with respect to the total weight of the food composition.

In another aspect of the present invention, the *Sargassum serratifolium* extract of the present invention may be included at a concentration of 0.1 μg/ml to 10000 μg/ml with respect to the food composition, and the compound separated from the *Sargassum serratifolium* extract (SHQ, SCM and SQA) may be included at a concentration of 0.1 μg/ml to 10000 μg/ml with respect to the food composition.

Such a *Sargassum serratifolium* extract or a compound separated therefrom (SHQ, SCM, and SQA), which is the active ingredient of the present invention, is derived from a natural material and has few side effects unlike chemicals, so that it can be safely used for long-term use for the purpose of imparting functionality of preventing or alleviating oxidative stress-related diseases.

Further, the present invention may be a health functional food for preventing or alleviating eye diseases, which includes a *Sargassum serratifolium* extract or a fraction thereof in an active ingredient.

In an aspect of the present invention, the *Sargassum serratifolium* extract may be a *Sargassum serratifolium* ethanol extract extracted with ethanol solvent, and the compound may be sargahydroquinoic acid (SHQ), sargaquinoic acid (SQA), or sagachromenol (SCM).

In another aspect of the present invention, the eye disease may be oxidative stress-related eye diseases, which include, for example, age-related macular degeneration, glaucoma, diabetic retinopathy, retinitis pigmentosa, choroidal neovascular membrane, uveitis, myopia degeneration, ocular tumor, central retinal vein occlusion, skin flushing, ocular neovascularization, central serous retinopathy, dry eye syndrome, central retinal artery occlusion, cystoid macular edema, and the like, but is not limited thereto.

The health functional food of the present invention may be produced and processed in the form of tablets, capsules, powders, granules, liquids, and pills for the purpose of preventing or alleviating eye diseases.

The term "health functional food" in the present invention refers to foods produced or processed using raw materials or components that have useful functionality in the human body according to the health functional food law or means that the food is ingested for the purpose of obtaining a beneficial effect for health use such as controlling nutrients or physiological action for the structure and function of the human body.

The health functional food of the present invention may include common food additives. The conformity of the "food additive" is determined, as long as there are no other regulations, in consideration with the standard and criteria of the corresponding item according to the general rule of the food additives codex and general tests approved by the Korean Ministry of Food and Drug Safety.

The items listed on the "food additives codex" include chemical compounds such as ketones, glycine, calcium citrate, nicotinic acid, and cinnamic acid; natural additives such as persimmon color, licorice extract, crystalline cellulose, kaoliang color and guar gum; and mixed preparations such as L-glutamic acid sodium preparations, alkalis additives for noodle, preservative preparations, tar color preparations.

For example, in order to produce a health functional food in a tablet form, a mixture of the *Sargassum serratifolium* extract or compound separated therefrom (SHQ, SCM and SQA) as an active ingredient of the present invention, excipients, binders, disintegrants, and other additives can be granulated using a conventional method, and then compression molding process is performed with lubricants. Alternatively, the mixture can be directly subjected to the compression molding process. In addition, when needed, the health functional food in a tablet form may include sweetening agents.

Among health functional foods in a capsule form, a hard capsule formulation can be produced by filling a conventional hard capsule with a mixture of the *Sargassum serratifolium* extract or compound separated therefrom (SHQ, SCM and SQA) as an active ingredient of the present invention and additives such as excipients; and a soft capsule formulation can be produced by filling a capsule support of gelatin with a mixture of the *Sargassum serratifolium* extract or compound separated therefrom (SHQ, SCM and SQA) as an active ingredient of the present invention and additives such as excipients. When needed, the soft capsule formulation can include plasticizers such as glycerin or sorbitol, coloring agents, and preservatives.

A health functional food in a pill form can be produced by molding a mixture of the *Sargassum serratifolium* extract or compound separated therefrom (SHQ, SCM and SQA) as an active ingredient of the present invention, excipients, binders, and disintegrants using well-known methods. When needed, the health functional food in a pill form can be coated with white sugar or other coating materials, or the surface thereof can be coated with starch, talc, or other materials.

A health functional food in a granule form can be produced by granulating a mixture of the *Sargassum serratifolium* extract or compound separated therefrom (SHQ, SCM and SQA) as an active ingredient of the present invention, excipients, binders, and disintegrants using well-known methods. When needed, the health functional food in a granule form can include flavoring agents and sweetening agents.

The health functional food containing the *Sargassum serratifolium* extract or compound separated therefrom (SHQ, SCM and SQA) as an active ingredient of the present invention has been experimentally proved to have the effect of protecting photoreceptor cells through the excellent anti-oxidative effects as shown in the following examples, and thus it is effective for preventing or alleviating oxidative stress-related eye diseases.

The health functional food may be beverages, meat, chocolates, foods, snack, pizza, ramen, other noodles, gums, candy, ice cream, alcoholic beverages, vitamin complexes, and health supplement foods.

Hereinafter, the present invention will be described in more detail with embodiments. These embodiments are intended to more particularly illustrate the present invention, but the scope of the present invention is not limited to these embodiments.

Example 1

Preparation of *Sargassum serratifolium* Extract

<1-1> Preparation of *Sargassum serratifolium* Ethanol Extract

*Sargassum serratifolium* used in the present invention was collected by scuba diving, which grows naturally in Gijang-gun, Busan or Tongyeong-si, Gyeongsangnam-do, Korea. Professor Chang Kyun Choi of Department of Ecological Engineering, Pukyong National University confirmed the species of *Sargassum serratifolium* from Gijang-gun, and Professor Kim Namgil of Department of Marine Bioscience of Gyeongsang National University confirmed the species of *Sargassum serratifolium* from Tongyeong-si. *Sargassum serratifolium* was naturally dried in the shady and light spot and was ground. 2 kg of the powder obtained was added to 8 L ethanol (95% ethanol). The mixture was reflux-condensed to be extracted at 70° C. for 3 hours 3 times. The resultant was filtered with an ultrafilter (Nitto Denko, Japan). The ethanol was extracted from the filtrate at 40° C. in a vacuum rotary evaporator. Thus, 200±25 g of crude extract was obtained as an extracted residue. Thus, the obtained *Sargassum serratifolium* ethanol extract was used as a sample in the following experiment while being stored at 4° C. in a refrigerator.

For reference, ultrafiltration is a process that may separate substances dissolved or dispersed in the liquid by particle size or molecular size, which separates particles in the middle region of microfiltration and reverse osmosis using pressure difference as a driving force. Ultrafiltration membranes have pore sizes in the range of about 10 Å to about 500 Å and are mainly used for the separation of saccharides, proteins, living body materials, and polymer substances with particle sizes of 1 nm to 0.1 μm. Its fundamental principle is the same as that of the microfiltration. However, the membrane structure of the microfiltration has a symmetric pore structure, but the ultrafiltration membrane has a dense layer structure of asymmetric structure so that the ultrafiltration can separate smaller particles compared with the microfiltration. In this experiment, ultrafiltration was carried out using a laboratory-scale Sehan ultrafiltration system (UF system, Sehan Tech, Korea). The Sehan ultrafiltration system was composed of a 20 L feed liquid tank, a feed liquid pump, a microfiltration cartridge, an ultrafiltration cartridge, and a pressure gauge for feed liquid and concentrate. Further, a hollow fiber membrane (MWCO=50 kDa) with an outer diameter of 50 mm, a length of 600 mm, and an area of 1 m$^2$ was used. In the present invention, the ultrafiltration was carried out according to the continuous concentration mode. The sample solution was fed to the membrane module using a pump, which was performed at a flow rate of 0.1 L msec at 23° C. and a transmembrane pressure drop (TMP) of 0.2 bar to 2.0 bar. In this experiment, tube-type membranes with MWCO=50 kDa were used to have effects of removing even minute contaminants, bacterial debris, and viruses from the ethanol extract.

<1-2> Preparation of n-Hexane Soluble Fraction from *Sargassum serratifolium* Ethanol Extract 50 g the *Sargassum serratifolium* ethanol extract prepared in Example 1-1 was dissolved in 1 L a mixed solvent of water and ethanol (9:1, v/v). The mixture was poured into a separatory funnel, and 1 L n-hexane having the same amount was added to the separatory funnel. Then, the separatory funnel was shaken, and they were equilibrated. Then, the upper portion of soluble n-hexane was collected, treated with sodium sulfate (anhydrous), filtered and concentrated. This procedure was repeated 5 more times to obtain 42 g n-hexane fraction.

Each of the fractions obtained was used as a sample for the following experiments while being stored at 4° C. in a refrigerator.

Example 2

Separation of Sargahydroquinoic Acid, Sargachromenol, and Sargaquinoic Acid from *Sargassum serratifolium* Ethanol Extract <2-1> Separation of Sargahydroquinoic Acid 15 g the *Sargassum serratifolium* ethanol extract prepared in Example <1-1> was dissolved in 1 L a mixed solvent of water and ethanol (9:1, v/v), placed in a separatory funnel, and n-hexane having the same amount was added to the separatory funnel. After equilibration, the upper portion of soluble n-hexane was collected, dehydrated with anhydrous sodium sulfate, and then concentrated to separate a n-hexane fraction. 12.2 g the separated n-hexane fraction was dissolved in 120 mL methanol. The mixture was filtered through a membrane filter, and then 200 μL was injected so that they were separated in four fractions by HPLC with a Phenomenex C18 (2) (15 μm, 21.2 mm×250 mm) column (See FIG. 1). A mixed solvent of methanol (A) and water (B) was used as the mobile phase of the chromatography, and the flow rate was set to 7 mL. The chromatography was set under a condition in which the column was washed at an initial concentration of A/B (90/10) to A/B (94/6) for 33 minutes, then A/B (94/6) to A/B (100/0) for 2 minutes, and A/B (100/0) for 10 minutes. Then, the column was equilibrated at a concentration of A/B (90:10) for 10 minutes. The chromatography was performed by automatic sample injection with Autosampler 50 to 100 times, thereby preparing the primary fraction of fraction No. 1 in a large amount.

Figure 2:
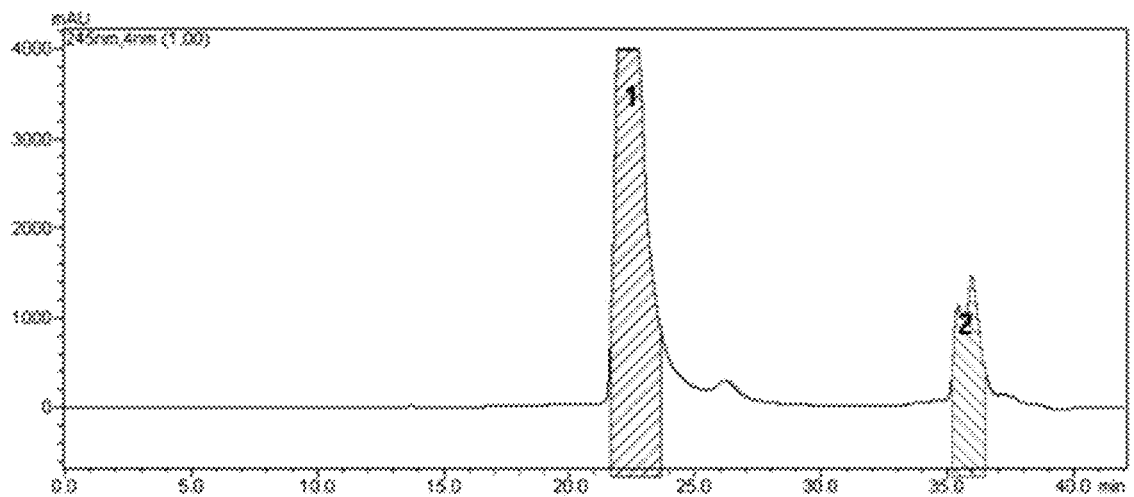
FIG. 2 illustrates a secondary fraction chromatogram of the fraction No. 1 of the four fractions obtained from a *Sargassum serratifolium* n-hexane fraction.

The same instrument and column were used to increase the purity of the primary fraction obtained in large quantities. The chromatography was set under a condition in which the column was washed at an initial concentration of A/B (85/15) to A/B (87/13) for 26 minutes, then A/B (87/13) to A/B (100/0) for 2 minutes, and A/B (100/0) for 6 minutes. Then, the column was equilibrated at a concentration of A/B (87:13) for 10 minutes. The chromatography was performed by automatic sample injection with Autosampler, thereby preparing the secondary fraction of fraction No. 1 having a higher purity (See FIG. 2).

Figure 3:
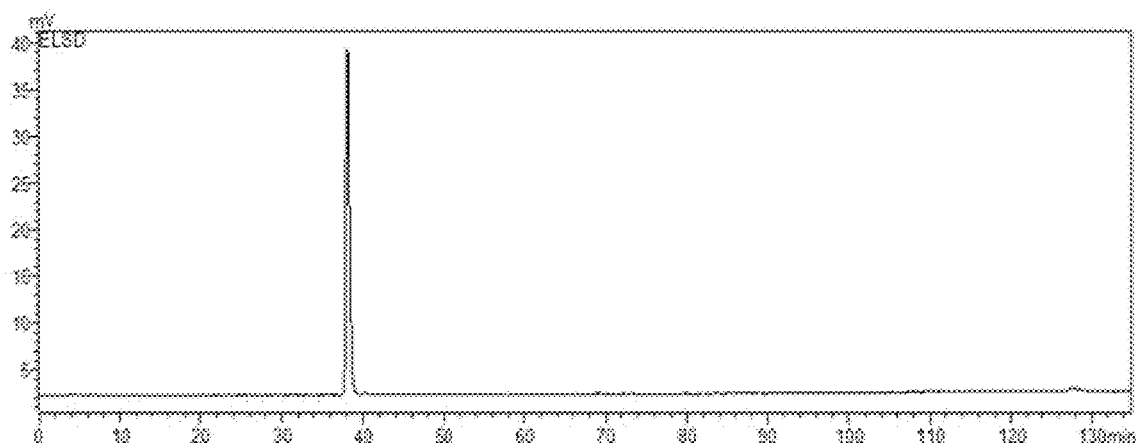
FIG. 3 illustrates a chromatogram of sargahydroquinoic acid identified by NMR analysis on a product obtained by purifying a secondary fraction of the fraction No. 1 of the four fractions obtained from a *Sargassum serratifolium* n-hexane fraction.

No. 1 of the secondary fractions of fraction No. 1 was purified by re-chromatography (523 mg) under the same conditions and analyzed with an analytical column (Phenomenex C18 (2), 3 μm, 3 mm×150 mm). The results indicate that it was a single material. The separated product was analyzed by NMR and found to be sargahydroquinoic acid (hereinafter, referred to as "SHQ") (See FIG. 3).

<Chemical formula 1>

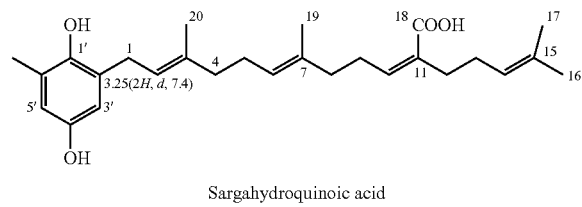

Sargahydroquinoic acid

<2-2> Separation of Sargachromenol

Figure 1:
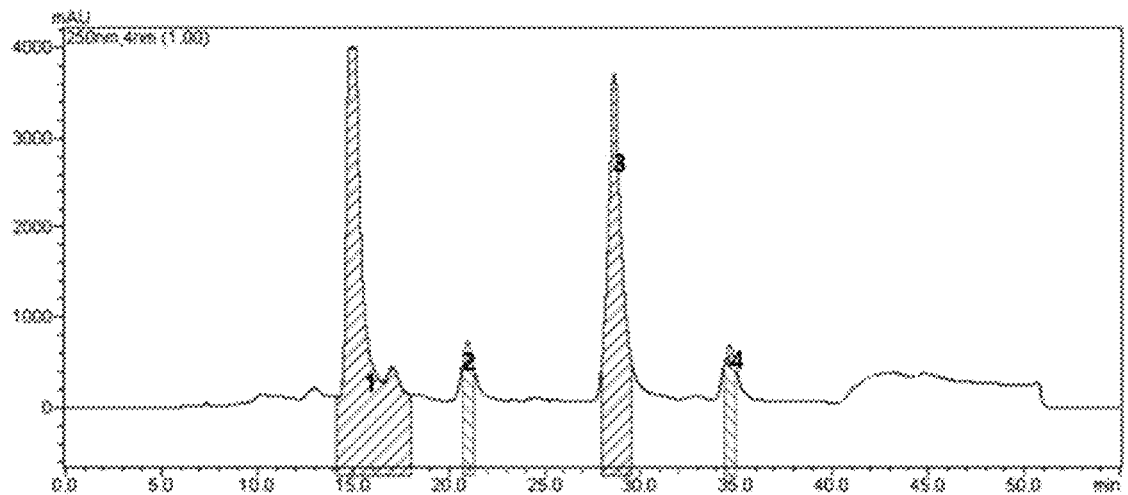
FIG. 1 illustrates four fraction chromatograms obtained from a *Sargassum serratifolium* n-hexane fraction.
Figure 4:
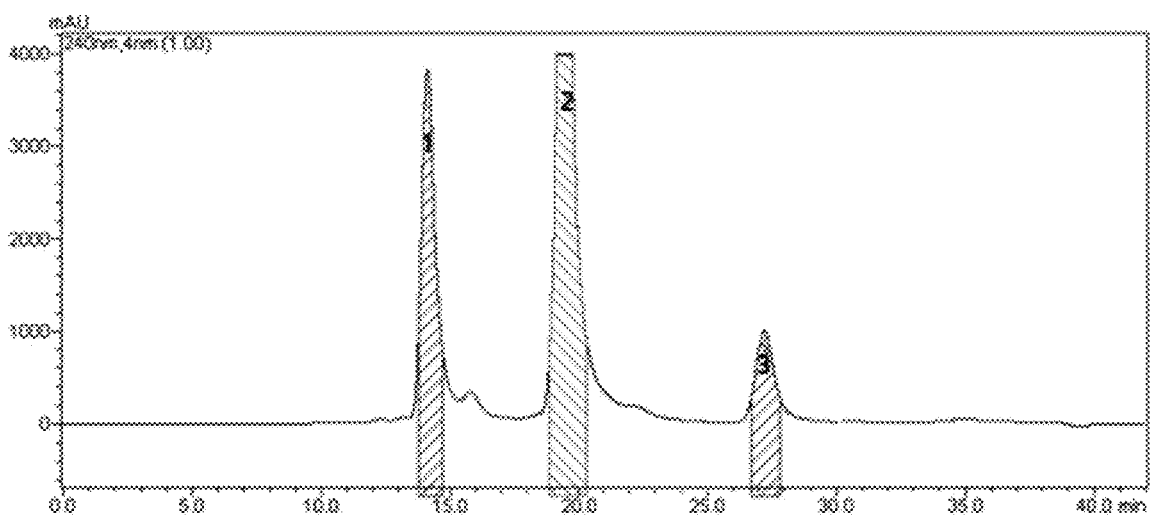
FIG. 4 illustrates the results of confirming three peaks in the secondary fraction chromatogram of the fraction No. 2 of the four fractions obtained from a *Sargassum serratifolium* n-hexane fraction.
Figure 5:
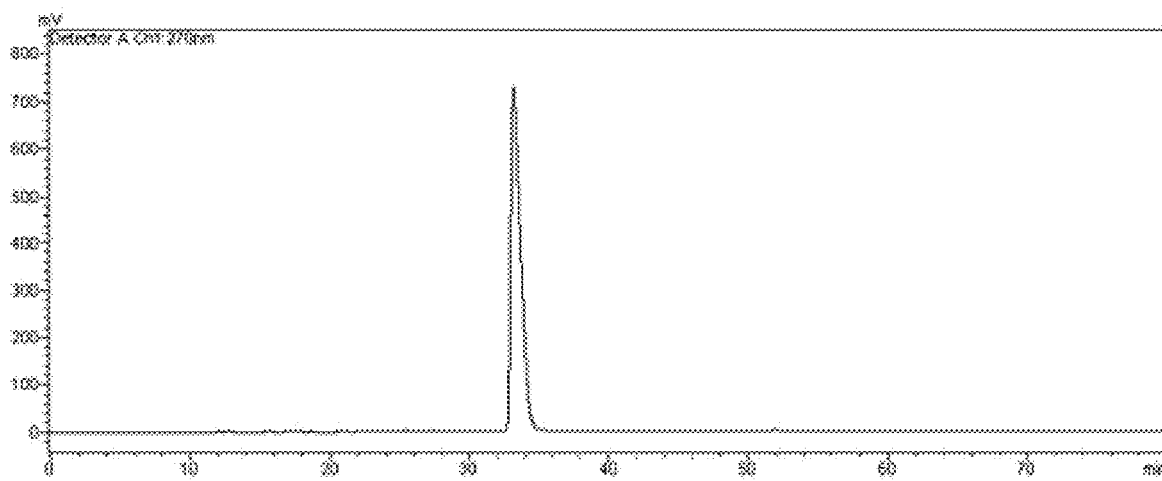
FIG. 5 illustrates a chromatogram of sagachromenol identified by NMR analysis on a product obtained by purifying 2nd peak of the secondary fraction of the fraction No. 2 of the four fractions obtained from a *Sargassum serratifolium* n-hexane fraction.

The fraction No. 2 in FIG. 1 was re-chromatographed using the same HPLC instrument and column as the fraction No. 1 in Example <2-1>. The chromatography was set under a condition in which the column was washed at an initial concentration of A/B (91.5/8.5) to A/B (92.2/7.8) for 26 minutes, then A/B (92.2/7.8) to A/B (100/0) for 2 minutes, and A/B (100/0) for 6 minutes. Then, the column was equilibrated at a concentration of A/B (91.5:8.5) for 10 minutes. The chromatography was performed by automatic sample injection with Autosampler 50 to 100 times, thereby preparing the secondary fraction of fraction No. 2 in a large amount (See FIG. 4). As illustrated in FIG. 4, the fraction No. 2 showed three peaks. Among them, the peak No. 2 (Frc2-2) was re-purified to obtain a chromatogram as illustrated in FIG. 5 (126 mg). The separated product was analyzed by NMR and found to be sargachromenol (hereinafter, referred to as "SCA") (See FIG. 5).

<Chemical formula 2>

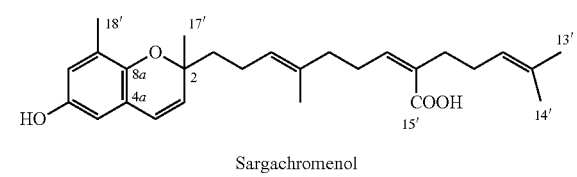

Sargachromenol

<2-3> Separation of Sargaquinoic Acid

Figure 6:
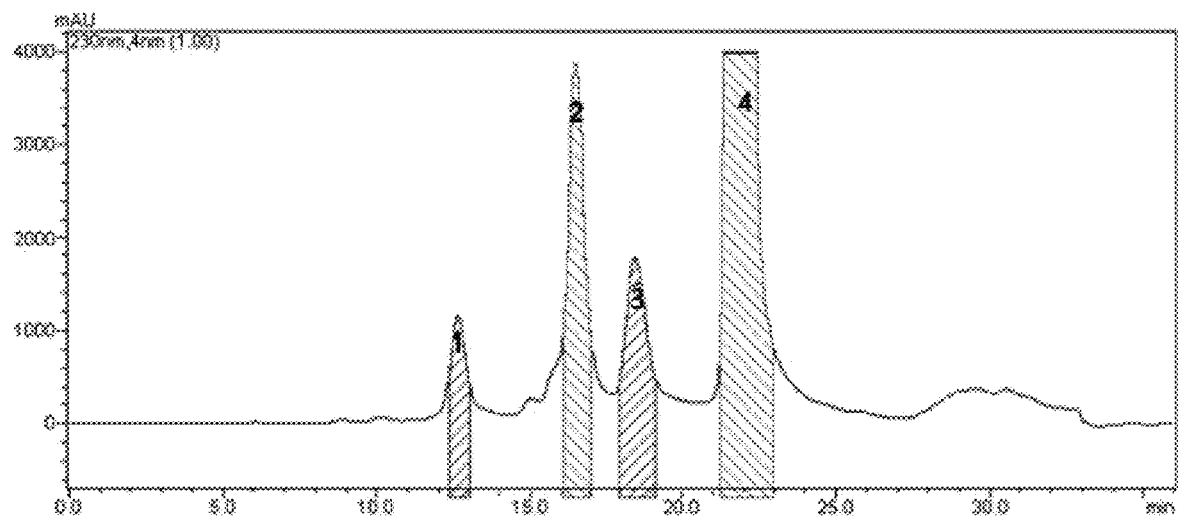
FIG. 6 illustrates the results of confirming four peaks in the secondary fraction chromatogram of the fraction No. 3 of the four fractions obtained from a *Sargassum serratifolium* n-hexane fraction.
Figure 7:
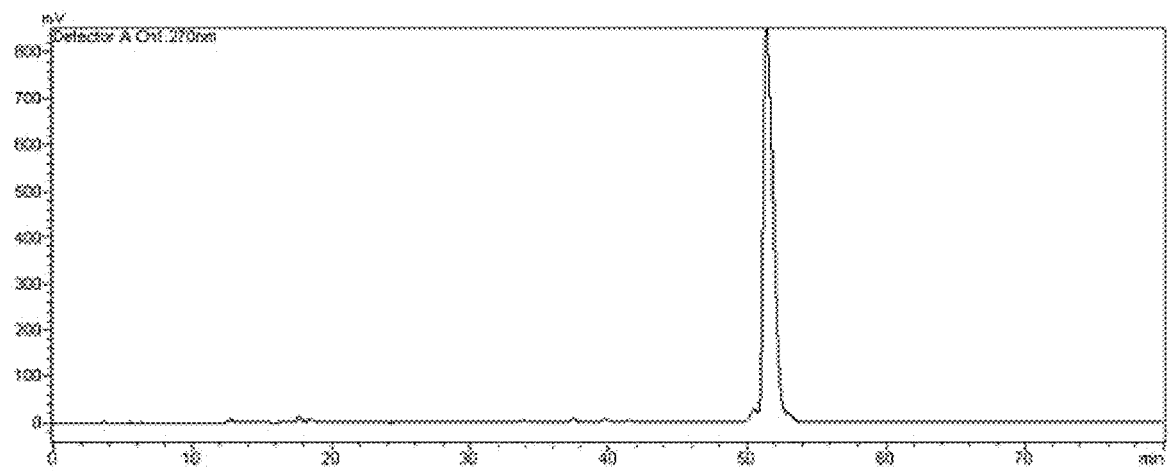
FIG. 7 illustrates a chromatogram of sargaquinoic acid identified by NMR analysis on a product obtained by purifying 4th peak of the secondary fraction of the fraction No. 2 of the four fractions obtained from a *Sargassum serratifolium* n-hexane fraction.

The fraction No. 3 in FIG. 1 was re-chromatographed using the same HPLC instrument and column as the fraction No. 1 in Example <2-1>. The chromatography was set under a condition in which the column was washed at an initial concentration of A/B (93.4/6.6) to A/B (93.8./6.2) for 20 minutes, then A/B (93.8/6.2) to A/B (100/0) for 2 minutes, and A/B (100/0) for 6 minutes. Then, the column was equilibrated at a concentration of A/B (93.8:6.2) for 10 minutes. The chromatography was performed by automatic sample injection with Autosampler 50 to 100 times, thereby preparing the secondary fraction of fraction No. 3 in a large amount (See FIG. 6). As illustrated in FIG. 6, the fraction No. 3 showed four peaks. Among them, the peak No. 4 (Frc3-4) was re-purified to obtain a chromatogram as illustrated in FIG. 7 (171 mg). The separated product was analyzed by NMR and found to be sargaquinoic acid (hereinafter, referred to as "SQA") (See FIG. 7).

<Chemical formula 3>

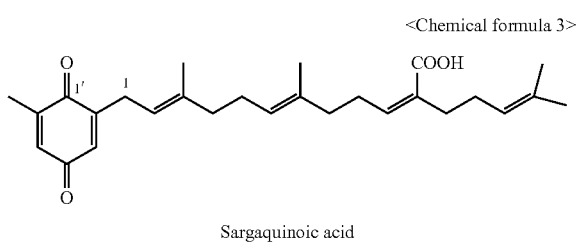 [SMILES: CC(C)=CCC/C(=C/CC/C(C)=C/CC/C(C)=C/CC1=CC(=O)C=C(C)C1=O)C(=O)O]

Sargaquinoic acid

Experimental Example 1

Evaluation of Cytotoxicity of *Sargassum serratifolium* Ethanol Extract and n-Hexane Fraction Thereof of the Present Invention RAW 264.7 cells ($5 \times 10^4$ cells/well) were treated with the *Sargassum serratifolium* ethanol extract or hexane fraction thereof, respectively, of the present invention prepared in Example 1, and cultured in DMEM medium for 24 hours. 95 μL the medium and 5 μL the MTS solution were placed in a 96-well plate and were reacted for 3 hours. Then, the absorbance thereof was measured at 490 nm using a microplate reader. The experiments were repeated three times, and the mean value thereof was used as its measurement value.

As illustrated in FIG. 8, the results indicate that the cytotoxicity of *Sargassum serratifolium* ethanol extract or hexane fraction thereof of the present invention to the macrophage line (RAW 264.7 cells) did not show up to a concentration of 8 μg/mL.

Experimental Example 2

Antioxidative Activity of *Sargassum serratifolium* Ethanol Extract and n-Hexane Fraction Thereof of the Present Invention Nitric oxide, reactive oxygen species (ROS), antioxidative activity by DPPH method, ABTs antioxidative activity, and hydroxyl radical were measured so as to evaluate the antioxidative activity of *Sargassum serratifolium* ethanol extract and hexane fraction thereof of the present invention prepared in Example 1.

<2-1> Measurement of Nitric Oxide

RAW 264.7 cells ($7 \times 10^4$ cells/well) were inoculated into 96-well plates using DMEM medium. New medium containing samples (*Sargassum serratifolium* ethanol extract or hexane fraction thereof of the present invention prepared in Example 1) and LPS (1 μg/mL) were co-treated and were cultured for 24 hours. The Griess reagent was used, so that the amount of NO produced was measured in the form of $NO^{2-}$ present in the cell culture medium. 100 μL the cell culture supernatant and 100 μL Griess reagent [1% sulfanilamide, 0.1% naphthyl ethylenediamine in 5% phosphoric acid] were mixed and reacted on a 96-well plate for 10 minutes. Then, the absorbance thereof was measured at 540 nm using an ELISA reader. Standard concentration curves were obtained by serial dilution of sodium nitrite ($NaNO_2$).

As illustrated in FIG. 9, the results show that the production of nitric oxide (NO) induced by lipopolysaccharide (LPS) was decreased treatment-concentration dependently in the experimental group treated with the *Sargassum serratifolium* ethanol extract and hexane fraction thereof in macrophages, respectively. The $EC_{50}$ values of the ethanol extract and hexane fraction were 1.72 μg/mL and 1.51 μg/mL, respectively.

<2-2> Measurement of Intracellular Reactive Oxygen Species

DCFH-DA was used to measure the amount of active oxygen so as to examine the inhibitory effect of *Sargassum serratifolium* extract on the production of reactive oxygen species (RAW 264.7 cells). Samples (*Sargassum serratifolium* ethanol extract or hexane fraction thereof of the present invention prepared in Example 1) and LPS (1 μg/mL) were co-treated and were cultured for 2 hours. Then, they were treated with 20 μM DCFH-DA and were cultured for 30 minutes. Thereafter, the cell culture supernatant was collected and measured by spectrofluorometry at an excitation wavelength of 485 nm and a radiation wavelength of 523 nm.

As illustrated in FIG. 10, the results show that the production of reactive oxygen species induced by lipopolysaccharide (LPS) was decreased treatment-concentration dependently in the experimental group treated with the *Sargassum serratifolium* ethanol extract and hexane fraction thereof in macrophages, respectively. The $IC_{50}$ values of the ethanol extract and hexane fraction were 0.92±0.09 μg/mL and 0.88±0.08 μg/mL, respectively.

<2-3> Measurement of Antioxidative Activity by DPPH Method

The DPPH method (Blois, M. S.: Antioxidant determination by the use of a stable free radical, Nature, 26, 1199-1200, 1958) was used to measure the antioxidant effect of *Sargassum serratifolium* in vitro. The DPPH (1,1-diphenyl picrylhydrazyl) method is a method of measuring the antioxidative effect by hydrogen donating ability depending on the degree of discoloration of deep purple color by reduction due to a physiologically active substance having an antioxidative activity such as tocopherol, ascorbate, flavonoid compounds, aromatic amines, Maillard-type browning agent and peptide. For the measurement, 100 μl DPPH having a concentration of 200 μM and 100 μl the sample were mixed in a 96-well plate, and they reacted at room temperature for about 30 minutes. Then, the absorbance thereof was measured at 517 nm using a microplate reader. BHT was used as a positive control. The concentration thereof was compared to the same as that of the sample.

DPPH radical scavenging activity was calculated by the method as described below.

Radical scavenging activity (%)=$(A_{DPPH}-A_{sample})/A_{DPPH} \times 100$

As shown in Table 1, the results show that $IC_{50}$ values of *Sargassum serratifolium* ethanol extract and hexane fraction thereof were 11.17±0.42 μg/mL and 9.05±0.21 μg/mL, respectively, and these values were lower than those of BHT used as a positive control (See Table 1).

<2-4> ABTs Assay

The ABTs assay is similar to the DPPH assay but differs in that antioxidative activity is measured by generating free radicals through chemical reactions. ABTs are reacted with potassium persulfate to generate ABTs anion radicals, which react with H-donors such as phenolic compounds to be converted to colorless ABTs. Accordingly, the degree of antioxidative activity may be determined by measuring the amount of ABTs consumed by reacting with a sample containing a phenolic compound.

ABTs antioxidative activity was measured by partially modified Van den Berg (1999) and others using the discoloration of ABTs radical-specific green color by antioxidants.

Potassium persulfate was added to 7 mM ABTS solution at a final concentration of 2.4 mM. They reacted in the dark for 12 hours to 16 hours at R/T so as to produce ABTs cations. The resulting ABTs cation was diluted to be used, having an absorbance value of 0.7±0.02. 10 µL of the sample was treated with 190 µL ABTs+ working solution and reacted for 6 minutes in a 96-well plate. The absorbance thereof was measured at 732 nm. The radical scavenging activity was calculated from the measured values as follows. BHT was used as a positive control. The antioxidant ability of the sample is determined by the $IC_{50}$ value in which 50% of ABTs was reduced.

Percentage inhibiting activity $I$ (%)=$(A_{control}-A_{sample})/A_{control} \times 100$ $A_{control}$: Control (blank sample)
$A_{control}$: Sample measurement value As shown in Table 1, the results show that $IC_{50}$ values of *Sargassum serratifolium* ethanol extract and hexane fraction thereof were 17.44±3.1 µg/mL and 14.69±3.4 µg/mL, respectively, and these values were somewhat higher than those of BHT used as a positive control (See Table 1).

<2-5> Hydroxyl Radical Scavenging

Hydroxyl radicals (—OH) are the most reactive radicals among oxygen radicals, which occur during aerobic metabolism in the human body. These radicals damage peripheral cells to create collateral living body molecules. A deoxyribose test was performed so as to measure the ability to scavenge hydroxyl radicals. Hydroxyl radicals attack deoxyribose to create small fragments. Some of which are pink when added with TBA (thiobarbituric acid) under an acidic pH environment, so the degree of damage by hydroxyl radicals is measured by absorbance at 532 nm.

Experimental methods described in Chandini, Ganesan, and Bhaskar (Chandini, S. K., Ganesan, p., and Bhaskar, N. (2008) In vitro antioxidant activities of three selected brown seaweeds of India. Food Chemistry, 107, 707-713) were modified to be used. This reaction used 20 mM phosphate buffer (pH 7.4). Ferric chloride ($FeCl_3$) and EDTA (ethylenediaminetetraacetic acid), respectively, were dissolved as to be 1 mM, and deoxyribose, a reaction substrate, was added to be 2.8 mM, thereby preparing a working solution. 1 ml the sample to be measured was mixed with the working solution, and 0.1 ml ascorbic acid (1 mM) is added to form Fe2+–EDTA mixture which is an oxidized form of ferric chloride ($FeCl_3$) and ethylenediamine tetraacetic acid (EDTA). Then, 0.5 ml of 20 mM hydrogen peroxide ($H_2O_2$) was added to form Fe3+–EDTA and HO radical. They were then incubated at 37° C. for 1 hour. After the incubation, 1 ml of 2.8% Trichloroacetic acid (TCA) and 1% TBA, respectively, were added. The mixture was boiled in boiling water at 100° C. for 30 minutes. The absorbance thereof was measured. BHT (2 µg/ml to 25 µg/ml) was used as a positive control.

Hydroxyl radical scavenging ability (%)=$(A_{control}-A_{sample})/A_{control} \times 100$ $A_{control}$: Control (blank sample)
$A_{control}$: Sample measurement value As shown in Table 1, the results show that $IC_{50}$ values of *Sargassum serratifolium* ethanol extract and hexane fraction thereof were 1.12±0.15 µg/mL and 1.08±0.19 µg/mL, respectively. These values indicate that the antioxidative activity thereof was showed at a lower concentration compared to BHT used as a positive control (See Table 1).

TABLE 1

Antioxidant activity of *Sargassum serratifolium* ethanol extract and hexane fraction thereof

|  | DPPH ($IC_{50}$, µg/ml) | ABTs ($IC_{50}$, µg/ml) | OH radical ($IC_{50}$, µg/ml) |
| --- | --- | --- | --- |
| *Sargassum serratifolium* | 11.17 ± 0.42 | 17.44 ± 3.1 | 1.12 ± 0.15 |
| Hexane fraction of *Sargassum serratifolium* | 9.05 ± 0.21 | 14.69 ± 3.4 | 1.08 ± 0.19 |
| BHT (Control) | 11.18 ± 0.15 | 7.77 ± 0.74 | 1.675 ± 0.21 |

Experimental Example 3

Evaluation of Cytotoxicity of *Sargassum serratifolium* Ethanol Extract and Compounds Separated Therefrom (Sargahydroquinoic Acid (SHO), Sargachromenol (SCM), and Sargaquinoic Acid (SOA)) of the Present Invention on 661W Photoreceptor Cells In this experiment, the cytotoxicity of *Sargassum serratifolium* ethanol extract and the compounds separated therefrom prepared in Examples 1 and 2 to 661W photoreceptor cells was confirmed. The 661W photoreceptor cells are cell lines established by Dr. Al-Ubaidi. Dr. Al-Ubaidi supplied the cells, which were used in the experiment.

661W photoreceptor cells were cultured in 96-wells at a concentration of $3 \times 10^3$ cells/well. Then, they were treated with 1.0 µg/ml *Sargassum serratifolium* ethanol extract or compounds separated therefrom (sargahydroquinoic acid (SHQ), sargachromenol (SCM), and sargaquinoic acid (SQA)) at a concentration of 1.0 µM and cultured for 24 hours. Then, the medium was replaced with medium containing MTS reagent. Then, they were cultured for 1 hour. Cell viability was measured by measuring the absorbance at 490 nm and comparing the results. The cell viability was analyzed by Celltiter[96] Aqueous One solution assay kit (Promega).

As illustrated in FIGS. 11 and 12, the results indicate that no cytotoxicity was observed in the 661W photoreceptor cells in both *Sargassum serratifolium* ethanol extract (1 µg/ml) and the compound separated therefrom (1 µM). For reference, there was no cytotoxicity of *Sargassum serratifolium* ethanol extract up to a concentration of 2 µg/ml. There were also no cytotoxicity of sargahydroquinoic acid up to a concentration of 2.5 µM, sargachromenol up to a concentration of 2.5 µM, and sargaquinoic acid up to a concentration of 1.0 µM.

Experimental Example 4

Protective Effect of *Sargassum serratifolium* Ethanol Extract and Compounds Separated Therefrom (Sargahydroquinoic Acid (SHO), Sargachromenol (SCM), and Sargaquinoic Acid (SOA)) of the Present Invention on 661W Photoreceptor Cells from Oxidative Stress <4-1> Effect on the Cell Viability of 661W Cells Under Oxidative Stress In order to examine the protective effect of the *Sargassum serratifolium* ethanol extract and the compounds separated therefrom of the present invention prepared in Examples 1 and 2 on 661W photoreceptor cells, it is examined how the *Sargassum serratifolium* ethanol extract and the compounds separated therefrom of the present invention effect on the death of 661W photoreceptor cells treated with atRAL.

In other words, the atRAL is an intermediate metabolite of the visual cycle and is an aldehyde-type compound. The atRAL may induce excessive oxidative stress in cells. Therefore, when 661W photoreceptor cells were treated with the atRAL compound to induce the oxidative stress, the protective effect of the *Sargassum serratifolium* ethanol extract and the compound separated therefrom of the present invention on 661W photoreceptor cells was examined.

In detail, 661W photoreceptor cells were cultured in 96-wells at a concentration of $3 \times 10^3$ cells/well and treated with atRAL having a concentration of 1.8 μM (Sigma Aldrich, St. Louis, Mo., USA) for 24 hours. Then, the medium was replaced with medium containing MTS reagent, and they were cultured for 1 hour. The absorbance thereof was measured at 490 nm, and the results were compared to determine cell viability. The cell viability thereof was measured by Celltiter$^{96}$ Aqueous One solution assay kit (Promega).

As illustrated in FIG. 13, the results indicate that the cell viability of 661W photoreceptor cells was reduced by about 55% in the only atRAL-treated group, whereas the cell viability in the experimental group treated with 0.5 μg/mL of *Sargassum serratifolium* ethanol extract and atRAL was increased by about 25% compared to the experimental group treated with the only atRAL.

Further, the cell viability of 661W photoreceptor cells was more than 90% in the experimental group treated with 0.5 μM sargahydroquinoic acid (SHQ), sargachromenol (SCM), and sargaquinoic acid (SQA), respectively, so that no significant difference was found between the atRAL-treated group and the untreated group. The results demonstrate that the compounds derived from *Sargassum serratifolium* of the present invention have a very high protection effect on 661W photoreceptor cells.

In sum, it was concluded that the *Sargassum serratifolium* ethanol extract and the compounds separated therefrom of the present invention had the effect of protecting the photoreceptor cells within the range of showing no cytotoxicity.

<4-2> Inhibitory Effect on Reactive Oxygen Species in 661W Cells Under Oxidative Stress In order to check whether *Sargassum serratifolium* ethanol extract and the compounds separated therefrom of the present invention prepared in Examples 1 and 2 have the antioxidant activity in 661W photoreceptor cells under oxidative stress, the inhibitory effect of the reactive oxygen species in 661W photoreceptor cells treated with atRAL was observed in this experiment.

For reference, 2',7'-dichlorodihydrofluorescein diacetate (DCFH-DA) converts to DCF, which expresses fluorescence in response to oxidative stress in cells. Therefore, the expression of DCF in cells is used as an indicator of the degree of oxidative stress.

In order to examine the antioxidative effect of the *Sargassum serratifolium* ethanol extract and the compounds separated therefrom of the present invention, atRAL (1.8 μM) and *Sargassum serratifolium* ethanol extract (0.5 μg/mL), sargachromenol (0.5 μM), sargahydroquinoic acid (0.5 μM) or sargaquinoic acid (1.0 μM) were added to medium mixed with DCFH-DA (20 μM), and the photoreceptor cells were treated with them and cultured for 30 minutes. Then, the cells were washed with PBS, and the cells were recovered. The cells expressing the fluorescence were measured using flow cytometry.

As illustrated in FIG. 14, the results demonstrate that the cells treated with atRAL only had a fluorescence expression level having about 80% higher than that of the control group. In the group treated with atRAL and *Sargassum serratifolium* ethanol extract (0.5 μg/mL), the fluorescence expression level was reduced by about 75% compared to the group treated with atRAL only. In the groups treated with atRAL and sargachromenol (0.5 μM), sargahydroquinoic acid (0.5 μM) or sargaquinoic acid (1.0 μM), the fluorescence expression levels were reduced by 76%, 77%, and 73%, respectively, and there was no difference from the control group untreated with atRAL.

Therefore, the *Sargassum serratifolium* ethanol extract and compound separated therefrom were found to effectively inhibit atRAL-induced oxidative stress, thereby protecting photoreceptors.

<4-3> Inhibitory Effect on Malondialdehyde in 661W Cells Under Oxidative Stress

In order to check whether the *Sargassum serratifolium* ethanol extract and the compounds separated therefrom of the present invention prepared in Examples 1 and 2 have antioxidant activity in 661W photoreceptor cells under oxidative stress, the inhibitory level of malondialdehyde (MDA) production in 661W photoreceptor cells treated with atRAL was observed in this experiment. For reference, the malondialdehyde (MDA) is the result of lipid peroxidation by excessive oxidative stress in cells, and thus the amount of MDA in cells is a factor to measure the degree of oxidative stress.

In detail, samples of each of *Sargassum serratifolium* ethanol extract and the compounds separated therefrom were mixed with a specific amount of atRAL (1.8 μM) and *Sargassum serratifolium* ethanol extract (0.5 μg/mL), sargachromenol (0.5 μM), sargahydroquinoic acid (0.5 μM) or sargaquinoic acid (1.0 μM). The photoreceptor cells were treated with mixtures. Then, they were cultured for 2 hours. The cells were then washed with PBS and the intracellular proteins were recovered. The number of proteins denatured by the lipid peroxides in cells was analyzed by protein immunoassay using MDA immunoblot kit (Cell biolabs).

As illustrated in FIG. 15, the results indicate that the cells treated with atRAL only showed an increase in expression level of protein denatured by MDA compared with the control, whereas the group treated with atRAL and *Sargassum serratifolium* ethanol extract having 0.5 μg/mL of the present invention has decreased expression level of MDA peroxidase protein compared with the group treated with atRAL only. The expression level of MDA peroxidase protein was similarly decreased in the experimental groups treated with atRAL and compounds separated from *Sargassum serratifolium* ethanol extract, respectively.

Therefore, it is determined that the *Sargassum serratifolium* ethanol extract and compound separated therefrom effectively inhibit atRAL-induced oxidative stress so that the photoreceptors are protected by inhibiting peroxidation of cell membrane lipid component.

Preparation Example 1

Production of Functional Cosmetic Composition with Antioxidative Activity of the Present Invention <1-1> Toner (Skin)

The toner (skin) containing the *Sargassum serratifolium* ethanol extract or hexane fraction of the present invention was produced in the following composition ratio using a conventional method.

TABLE 2

Example of toner formulation of the present invention

| Composition | Content (weight %) |
| --- | --- |
| *Sargassum serratifolium* ethanol extract or hexane fraction | 1 to 3 |
| Glycerin | 5.0 |
| 1,3-Butylene glycol | 3.0 |
| REG 1500 | 1.0 |
| Allantoin | 0.1 |
| DL-Panthenol | 0.3 |
| EDTA-2Na | 0.02 |
| Benzophenone-9 | 0.04 |
| Sodium hyaluronate | 5.0 |
| Ethanol | 10.0 |
| Octyldodeceth-16 | 0.2 |
| Polysorbate 20 | 0.2 |
| Unicide-U13 | 0.01 |
| Flavor | Trace |
| Distilled water | Residue |
| Total | 100 |

<1-2> Toner (Lotion)

The toner (lotion) containing the *Sargassum serratifolium* ethanol extract or hexane fraction of the present invention was produced in the following composition ratio using a conventional method.

TABLE 3

Example of toner formulation of the present invention

| Composition | Content (weight %) |
| --- | --- |
| *Sargassum serratifolium* ethanol extract or hexane fraction | 1 to 3 |
| Glyceryl stearate SE | 1.5 |
| Cetearyl alcohol | 1.5 |
| Lanolin | 1.5 |
| Polysorbate 60 | 1.3 |
| Sorbitan stearate | 0.5 |
| Hardened vegetable oil | 4.0 |
| Mineral oil | 5.0 |
| Trioctanoin | 2.0 |
| Dimethicone | 0.8 |
| Tocopherol acetate | 0.5 |
| Carboxyvinyl polymer | 0.12 |
| Glycerin | 5.0 |
| 1,3-Butylene glycol | 3.0 |
| Sodium hyaluronate | 5.0 |
| Triethanolamine | 0.12 |
| Unicide-U 13 | 0.02 |
| Flavor | Trace |
| Distilled water | Residue |
| Total | 100 |

<1-3> Nourishing Cream

The nourishing cream containing the *Sargassum serratifolium* ethanol extract or hexane fraction of the present invention was produced in the following composition ratio using a conventional method.

TABLE 4

Example of nourishing cream formulation of the present invention

| Composition | Content (weight %) |
| --- | --- |
| *Sargassum serratifolium* ethanol extract or hexane fraction | 1 to 10 |
| Lipophilic monostearic acid glycerin | 1.5 |
| Cetearyl alcohol | 1.5 |
| Stearic acid | 1.0 |
| Polysorbate 60 | 1.5 |
| Sorbitan Stearate | 0.6 |
| Isostearyl isostearate | 5.0 |
| Squalene | 5.0 |
| Mineral oil | 35.0 |
| Dimethicone | 0.5 |
| Hydroxyethyl cellulose | 0.12 |
| Glycerin | 6.0 |
| Triethanolamine | 0.7 |
| Unicide-U13 | 0.02 |
| Flavor | Trace |
| Distilled water | Residue |
| Total | 100 |

<1-4> Massage Cream

The massage cream containing the *Sargassum serratifolium* ethanol extract or hexane fraction of the present invention was produced in the following composition ratio using a conventional method.

TABLE 5

Example of massage cream formulation of the present invention

| Composition | Content (weight %) |
| --- | --- |
| *Sargassum serratifolium* ethanol extract or hexane fraction | 1 to 3 |
| Propylene glycol | 6 |
| Glycerin | 4.0 |
| Triethanolamine | 0.5 |
| Wax | 2.0 |
| Tocopheryl acetate | 0.1 |
| Polysorbate 60 | 3.0 |
| Sorbitan sesquioleate | 2.5 |
| Cetearyl alcohol | 2.0 |
| Liquid paraffin | 30.0 |
| Carboxyvinyl polymer | 0.5 |
| Flavor | Trace |
| Distilled water | Residue |
| Total | 100 |

<1-5> Pack

The pack containing the *Sargassum serratifolium* ethanol extract or hexane fraction of the present invention was produced in the following composition ratio using a conventional method.

TABLE 6

Example of pack formulation of the present invention

| Composition | Content (weight %) |
|---|---|
| *Sargassum serratifolium* ethanol extract or hexane fraction | 1 to 3 |
| Glycerin | 10.0 |
| Betaine | 5.0 |
| REG 1500 | 2.0 |
| Allantoin | 0.1 |
| DL-panthenol | 0.3 |
| EDTA-2Na | 0.02 |
| Benzophenone-9 | 0.04 |
| Hydroxyethylcellulose | 0.1 |
| Sodium hyaluronate | 80. |
| Carboxyvinyl polymer | 0.2 |
| Triethanolamine | 0.18 |
| Octyldodecanol | 0.3 |
| Octyldodeceth-16 | 0.4 |
| Ethanol | 6.0 |
| Unicide-U13 | 0.01 |
| Flavor | Trace |
| Distilled water | Residue |
| Total | 100 |

As described above, the present invention has been described to focus on the preferred embodiments. Those of ordinary skill in the art to which the present invention belongs may understand that the present invention may be carried out in various forms without departing from the essential scope of the present invention. Therefore, the disclosed embodiments should be considered in an illustrative rather than a limited purpose. The scope of the present invention is set forth in the following claims, rather than the foregoing description, and all differences within the scope of equivalents thereof should be construed as being included in the present invention.

The invention claimed is:

1. A method of protecting photoreceptor cell in vitro or in a subject in need thereof from antioxidative activity comprising contacting the photoreceptor cell with a therapeutically effective amount of a composition comprising a *Sargassum serratifolium* extract or a compound separated therefrom as an active ingredient.

2. The method of claim 1, wherein the extract is an extraction of the *Sargassum serratifolium* plant with a solvent comprising ethanol.

3. The method of claim 1, wherein the compound is sargahydroquinoic acid, sargaquinoic acid, or sagachromenol.

4. The method of claim 1, wherein the extract is an extraction of the *Sargassum serratifolium* plant with a solvent selected from the group consisting of lower alcohols having 1 to 4 carbon atoms, ethyl acetate, acetone, water, and hexane.

* * * * *